United States Patent [19]

Thiele

[11] 4,196,218

[45] * Apr. 1, 1980

[54] INJECTABLE SOLUTIONS AND PROCESSES OF USING SUCH

[75] Inventor: Geraldine H. Thiele, New Oxford, Pa.

[73] Assignee: Oxford Hill, Ltd., New Oxford, Pa.

[*] Notice: The portion of the term of this patent subsequent to Jun. 26, 1990, has been disclaimed.

[21] Appl. No.: 890,239

[22] Filed: Mar. 27, 1978

Related U.S. Application Data

[63] Continuation of Ser. No. 724,943, Mar. 20, 1976, abandoned, which is a continuation of Ser. No. 483,010, Jun. 25, 1974, Pat. No. 3,982,017, which is a continuation-in-part of Ser. No. 369,236, Jun. 12, 1973, Pat. No. 3,924,000, which is a continuation-in-part of Ser. No. 123,830, Mar. 12, 1971, Pat. No. 3,767,812, Ser. No. 283,662, Aug. 25, 1972, Pat. No. 3,805,776, Ser. No. 283,663, Aug. 25, 1972, and Ser. No. 113,362, Feb. 8, 1971, said Ser. No. 283,662, and Ser. No. 283,663, each is a continuation-in-part of Ser. No. 123,830, Mar. 12, 1971, and Ser. No. 113,362, Feb. 8, 1971, said Ser. No. 123,830.

[51] Int. Cl.$^2$ .................... A61K 31/20; A61K 31/045
[52] U.S. Cl. ...................................... 424/318; 424/343
[58] Field of Search ......................................... 424/318

[56] References Cited

U.S. PATENT DOCUMENTS 3,982,017  9/1976  Thiele .................................. 24/318

*Primary Examiner*—Sam Rosen
*Attorney, Agent, or Firm*—Fisher, Christen & Sabol

[57] ABSTRACT

A liquefied composition which contains an effective amount of a non-necrotic sclerosing fatty acid salt, an effective amount of ethyl alcohol, a buffering agent, and a water carrier. The fatty acid salt is prepared from an unsaturated fatty acid having one double bond and from an alkali metal or an alkaline earth metal or an alkali metal compound or an alkaline earth metal compound. The liquefied composition has a pH between 9 and 11. The liquefied composition can be used for, among other things, faster healing of fractures, breaks and nonunions of bones without muscle atrophy, etc., by injecting the liquefied composition into the site of the fracture or nonunions. No cast is used.

10 Claims, 4 Drawing Figures

INJECTABLE SOLUTIONS AND PROCESSES OF USING SUCH

This application is a continuation application of Applicant's application Ser. No. 724,943, filed on Mar. 20, 1976 abandoned; Applicant's Ser. No. 724,943 is a continuation of Applicant's application Ser. No. 483,010, entitled "Injectable Solutions and Processes of Using Such", which was filed on June 25, 1974 now U.S. Pat. No. 3,982,017; Applicant's application Ser. No. 483,010 is a continuation-in-part application of Applicant's application Ser. No. 369,236, entitled, "Injectable Solution", which was filed on June 12, 1973 now U.S. Pat. No. 3,924,000; Applicant's application Ser. No. 369,236 (filed on June 12, 1973), is a continuation-in-part application of Applicant's application Ser. No. 113,362, titled "Method of Treating Bone Fractures and Non-Unions", which was filed on Feb. 8, 1971, and which is now U.S. Pat. No. 3,741,204, issued on June 26, 1973; Applicant's application Ser. No. 369,236 (filed on June 12, 1973) is a continuation-in-part application of Applicant's application Ser. No. 123,830, entitled "Non-Surgical Removal of Abnormal New Bone Proliferation", which was filed on Mar. 12, 1971, which is now U.S. Pat. No. 3,767,812, issued on Oct. 23, 1973, and which is a continuation-in-part application of Applicant's application Ser. No. 113,362, (filed Feb. 8, 1971); Applicant's application Ser. No. 369,236 (filed on June 12, 1973) is a continuation-in-part application of Applicant's application Ser. No. 283,662, entitled "Treatment of Non-Surgical Osteolysis of Bone", which was filed on Aug. 25, 1972, which is now U.S. Pat. No. 3,805,776, issued on Apr. 23, 1974, which is a continuation-in-part of Applicant's application Ser. No. 113,362 (filed on Feb. 8, 1971) and which is a continuation-in-part of Applicant's application Ser. No. 123,830 (filed on Mar. 12, 1971); Applicant's application Ser. No. 369,236 (filed on June 12, 1973) is a continuation-in-part application of Applicant's application Ser. No. 283,663, entitled "Method of Fusing Bones", which was filed on Aug. 25, 1972, which is a continuation-in-part application of Applicant's application Ser. No. 113,362 (filed on Feb. 8, 1971) and is a continuation-in-part application of Applicant's application Ser. No. 123,830 (filed on Mar. 12, 1971); Applicant's application Ser. No. 369,236 (filed on June 12, 1973), is a continuation-in-part application of Applicant's application Ser. No. 113,362 (filed on Feb. 8, 1971), is a continuation-in-part application of Applicant's application Ser. No. 123,830 (filed on Mar. 12, 1971), is a continuation-in-part application of Applicant's application Ser. No. 283,662 (filed on Aug. 25, 1972) and is a continuation-in-part application of Applicant's application Ser. No. 283,663 (filed Aug. 25, 1972); and Applicant's application Ser. No. 483,010 is a continuation-in-part of Applicant's application Ser. No. 283,662, entitled "Treatment of Non-Surgical Osteolysis of Bone", which was filed on Aug. 25, 1972, which is a continuation-in-part of Applicant's application Ser. No. 113,362 (filed on Feb. 8, 1971) and which is a continuation-in-part of Applicant's application Ser. No. 123,830 (filed on Mar. 12, 1971).

BACKGROUND OF THIS INVENTION

1. Field of this Invention

This invention relates to the fusion of bones, to the treatment of bone fractures, breaks and nonunions, and to the treatment of osteolysis of the region of bone around a metal object in or contacting the bone using a non-necrotic vascular sclerosing fatty acid compound.

2. Prior Art

Known vascular sclerosing agents include phenol, zinc sulphate, glucose, strong sodium chloride solution, tannic acid and extracts containing tannins, urea, quinine, resins and extracts containing them, mineral acids, the salts or soaps of the fatty acids of various oils, particularly cod liver oil, and psyllium seed oil, amine soaps of fatty acids, ethanol, dextrose and invert sugar.

U.S. Pat. No. 1,621,118 teaches producing serum by treating bacteria and/or their toxins with soluble salts of higher fatty acids, and injecting the resultant antigens into the system of man or animal. U.S. Pat. No. 1,936,456 discloses the use of sodium ricinoleate and a fluid vehicle to treat internal body surfaces which can only be reached through body orifices.

Ringbones, splints, bucked shins and osselets are four aliments which have been treated for years by two methods, namely, (1) firing and (2) blistering. These two methods of treatment are in unscientific, permanently scar what would otherwise be healthy tissue, and take long times to effect healing, even if such is achieved.

U.S. Pat. No. 3,551,554 teaches the use of dimethyl sulfoxide to enhance the penetration of certain chemical agents capable of eliciting a physiological effect through an external membrane barrier of a human or animal.

Attention is also drawn to: U.S. Pat. Nos. 3,223,083, 2,046,116, 2,090,456, 2,037,196, 1,936,457, 2,115,492, 1,767,041, 2,497,742, 2,115,491 and 3,030,951; Park, Richard D., "Chip Fractures***", J.A.V.M.A., Vol. 157, No. 10, (Nov. 15, 1970), pages 1305 to 1312; *Medical World News*, (Dec. 10, 1971), page 680; Bassett, C. A. L., "Electrical Effects In Bone", Scientific American, Vol. 213, No. 4, (Oct. 1965), pages 18 to 25; Rooney, James R., "Biomechanics of Lameness in Horses", (1969 Ed.), pages 148 and 171; *New and Nonofficial Remedies,* (1948), page 423; *The Pharmacopeia of U.S.A.* 16th Rev., (1960), pages 356, 678 and 679; *Webster's New International Dictionary,* 2nd Ed., Unbridged, (1950), page 427; Goubaux, A., and G. Barrier, "Exterior of the Horse", (1892); *Equine Medicine and Surgery,* especially pages 505 to 509; Adams, O. R., "Lameness in Horses", 2nd Ed., (1967), especially pages 163 and 201; *Hernia Technic—The Injection Treatement, G. D. Searle & Co., Chicago,* (1935), pages 2 to 4; Harlow, M. C. et al., "The Origin of Resting Bioelectric Potentials in the Rabbit Tibia", Surgical Forum, Vol. XXII (1971); Friedenberg, Z. B., et al., "Stimulation of Fracture Healing By Direct Current In the Rabbit Fibula", the J. of Bone and Joint Surgery, Vol. 53-A, (October 1971), pp. 1400–08; Friedenberg, Z. B., et al., "Electro-Osteograms of Long Bones of Immature Rabbits", J. of Dental Research, Vol. 50 (May-June 1971), pp. 635–39; Friedenberg, Z. B., et al., "Healing of Nonunion***", The J. of Trauma, Vol. 11(1971), pp. 883–85; and British Pat. Nos. 470,925 and 1,034,536.

BROAD DESCRIPTION OF THIS INVENTION

This invention involves an injectable liquefied composition comprised of a non-necrotic vascular sclerosing fatty acid compound and a liquid carrier, which is useful, for example, for the treatment of bone fractures, breaks and nonunions, for the fusing of bones, having surfaces in juxtaposition, and for the treatment of osteolysis of the region of bone around a metal object in or contacting said bone.

Preferably the fatty acid compound is a fatty acid salt, and preferably the fatty acid salt is prepared from an alkali metal or basic alkali metal compound, and a fatty acid. More preferably the non-necrotic vascular sclerosing fatty acid compound is sodium oleate or monoethanolamine oleate. The preferred liquid carrier is water. Preferably a buffering agent is present in the injectable liquefied composition and the preferred buffereing agent is sodium dihydrogen phosphate. The injectable liquefied composition is preferably in a dosage form and preferably the dosage contains between 0.1 and 10 c.c. More preferably the dosage contains between 0.5 and 5 cc. Preferably the injectable liquefied composition has a pH between 8 and 11, and more preferably has a pH between 9 and 10. Preferably the injectable liquefied composition contains a minor amount of ethanol. More preferably the injectable liquefied compositon contains 0.1 to 5 percent ethanol. A preferred composition contains sodium oleate, water, ethyl alcohol and sodium dihydrogen phosphate. Another preferred injectable liquefied compositions 1 to 10 percent of the non-necrotic fatty acid compound, enough buffering agent to adjust the pH to the stated preferred range and the remainder water.

The most preferred injectable liquefied composition is comprised of 5 percent of sodium oleate or monoethanolamine oleate. 1.5 percent of ethyl alchol, enough disodium hydrogen phosphate to adjust the pH to 9.8, and the remainder water.

The injectable liquefied composition of this invention can be used in a process of treating bone fractures breaks and non-unions of man and animal. The process includes: aligning (only when necessary) the bone parts to position for setting; and then injecting at least one dosage of the injectable liquefied composition comprised of a non-necrotic vascular sclerosing fatty acid compound and a liquid carrier into a site of the fracture, break or nonunion area of the bone until there is a substantially complete bone union. Preferably another dosage is injected a week or two after the first dosage and then every week or two thereafter, as needed, until there is a substantially complete bone union. Preferably each dosage of the injectable liquefied composition is injected into the site of the fracture, break or nonunion at its axis.

It is noted that while a liquefied composition is preferably injected, the ingredients can be in any form of a gel, cream, or the like which can be injected.

The term liquefied composition encompasses gel, cream and the like.

A cream or like of the non-necrotic vascular sclerosing fatty acid compound and an inert paste carrier can be injected into the fracture site. The cream has the viscosity, cohesive properties and adhesive properties to hold the non-necrotic vascular sclerosing agent in the fracture site, thereby providing continuous healing stimulation. When a carrier such as water is used, some of the liquefied composition is lost by seepage from the injection site or by migration through the medullary cavity or soft tissue surrounding the fractured bone. A faster healing is believed to be obtained when a cream is used. The use of a cream is preferred in some instances, and a thixotropic gel is most preferred when a cream is used. The gel may have a detrimental effect on the precallous hematoma; any retained gel material may interfer with the infusion of new osteoblasts; and any retained gel material may cause over-stimulation, resulting in excessive bone formation.

The preferred cream contains 5 percent by weight of sodium oleate, 0.1 percent by weight of sodium phosphate (monobasic, monohydrate), 1.5 percent by weight of ethanol, 5 percent by weight of methylcellulose (60 HG 4000 cps), enough sodium hydroxide to obtain a pH of 9.8 and the remainder water.

The useful carriers are described below.

Reduction of a fracture, heretofore, must be complimented by immobilization of a cast as compression is put into effect. Compression, per se, can only increase the mass, it cannot align. My theory is that a cast leading to compression and atrophy of muscle is not only undesirable, but in the case of the equine reduction in many bones is impossible. It is proven that by injecting a non-necrotic vascular sclerosing fatty acid compound at the axis of the fracture, chemically introduced "struts" give rise to sheer, and thus alignment. The lack of the cast not only eliminates atrophy of muscle, the complication of "lipping", but the movement of the bone against the tension of muscle insertion helps to promote the flow blood to and from the damaged area.

The injectable liquefied composition of this invention can be used to heal (treat) simple, compound comminuted, linear, green-stick, multiple, distracted and partial fractures as well as non-unions which have been in existance as long as one year. This invention can also be used for splints, diffused splints, and fusion of meta-carpals and/or meta-torsals in regards to the three bone weight bearing complex or any boney meaterial.

The use of the liquefied composition of this invention allows the healing of bone fractures, breaks and non-unions to be reduced from as long as 18 months to 8 to 10 weeks, sometims less.

The non-necrotic fatty acid compositions of this invention polarize the hematoma or blood clot.

The accepted four stages of the healing of fractures (including mosaic features) to date are: (1) Stage of haematoma formation, (2) Stage of Callus formation, (3) Stage of Consolidation, and (4) Remodeling of Callus.

This invention involves the use of the injectable liquefied composition of this invention to treat and heal and the process of using the injectable liquefied composition of this invention to treat and heal mosaic fractures of the bone and periosteum, which are commonly called "bucked shins" in horses and other minute fractures of the bone periosteum (such as, splints, osselets and ringbone). The injection is normally made at a number of points around the site of the mosaic fracture. The injection is made right into the mosaic bone fracture site, going through the tissue and the coagulated tissue. The mosaic fracture in a bucked shin is normally quite long and extend down most of the bone. Each set of injections normally takes 6 to 8 c.c. of the injectable liquefied compositions. One set of injection in that manner is normally all that is required to effect healing and curing. The use of the most preferred injectable liquefied composition is the preferred form of this method.

The injectable liquefied composition of this invention can be used in a process of fusing bones of man and animal. The process includes: aligning (only when necessary) the bones to position, so that the interfaces of the bones are in juxtaposition, for fusing; and then injecting at least one dosage of the injectable liquefied composition comprised of a non-necrotic vascular sclerosing fatty acid compound and a liquid carrier into the interface region between the bones. The injection is repeated, if necessary, until there is a substantially complete fusion of the bones. Preferably another dosage is injected a week or two after the first dosage and then every week or two thereafter, as needed, until there is a substantially complete fusion of the bones.

The injectable liquefied composition of this invention can be used to fuse bones to prevent the occurrence of trauma of bones and possible fracture, break or non-union of such bones. For example, the injectable liquefied composition of this invention can be used in the fusion of the meta-carpals and/or meta-tarsals in regards to the three bone weight bearing complex in horses. More specifically, the medial and lateral meta-carpal and/or meta-tarsal is fused to the main shaft of the leg in horses, particularly in race horses which suffer a great deal of trauma in the affected region. The injectable liquefied composition of this invention can also be to fuse bones together whenever needed for medical reasons, for example, when vertebra in the spinal column need to be fused together. Broadly, the injectable liquefied composition of this invention can be used to fuse any boney materials, such as, tendons and bone cartilages.

The fusion is usually completed in 8 to 10 weeks, sometimes less.

A cast or brace should not normally be used around the bone areas to be fused. A cast leads to compression and atrophy of muscle, which of course is undesirable. In the case of equines, the use of a cast in the case of certain bones is impossible. The injection of a non-necrotic vascular sclerosing fatty acid compound at the interface region of the bones to be fused quickly chemically introduces "struts", which aligns and fixes the bones in relationship to each other which means braces and casts usually do not have to be used. The lack of the cast only eliminates atrophy of muscles.

Bone is almost incompressible under normal loads. Trauma to the bone results from excessive loads to the bone, which is compressed during those periods, for example, in the legs of show and race horses. Fusion of certain bones in the legs of show and race horses prevents the occurence of such trauma and helps prevent leg fractures, breaks and non-unions.

When a non-necrotic vascular sclerosing fatty acid compound is injected into the interface region between bones a non-vascular environment, which is controlled by an electrical field, the appropriate ionic concentration charges the area and the fantastic selectivity of the osteogenic calls can, therefore, put down cartilage. (in a non-vascular bone is formed.) Struts of callus are laid down between the bone surfaces. Callus is comprised almost entirely of cartilage, and nature converts it into bone so that a permanent union can be established.

The injectable liquefied composition of this invention can also be used to fuse pieces of bone to other bones in order to form a spling in order to strengthen or protect the other bone from excessive force, pressure, compressive trauma, etc. The bones to which such splints are applied can be those which have been weakened for some reason or which nature has not made strong enough for the task to which man or animal has put it. A splint can also be applied to prevent movement of a joint (as it would involve fusing a piece of bone to two or more other bones). This invention can also be used to prepare diffused splints.

Bone is composed of living cells and an intercellular matrix that is impregnated with calcium salts. Calcium phosphate makes up about 80 percent of the mineral matter, with the remainder composed largely of calcium carbonate and magnesium phosphate. One hundred cc. of bone contain 10,000 mg. of calcium, as compared with 6 mg. of calcium per 100 cc. of blood. Thus, bone serves as a mineral reservoir which is either constantly being replenished or constantly being depleted.

Adult bone cells are found in the lacunae within the matrix of the bone. Throughout life, osteoblasts are found in the deep layer of periosteum surrounding the bone, in Haversian canals, and in the endosteum. These cells function in bone growth and in fracture and bone repair.

Ossification is the formation of true bone by the deposition of calcium salts in a matrix of osteoid tissue.

Bone (even in a fresh carcass) appears hard, dense, inelastic, and almost lifeless. Actually bone as a tissue is extremely responsive to environmental changes in blood supply and to changes in nutrition. Bone can decrease in size (atrophy), increase in size (hypertrophy), repair brakes, and rearrange its internal structure to best resist stresses strains. Under both normal and pathological conditions, bone can normally reshape itself according to good engineering principles to sustain a maximum of stress with a minimum of bone tissue.

Osteolysis is the softening, absorption and destruction of bony tissue. It is also commonly termed demineralization. When metal screws, pins and the like are used in bone, osteolysis often occurs, i.e., the bone rejects the metal screws, etc. Calcium, which is the major component of bone, migrates from the region of the bone around the screws and deposits on the screws. The region from which the migration occurs becomes soft and spongy. The ossifluent regions are returned to normal bone by treatment using the injectable liquefied composition of this invention.

The inveniton involves injectable liquefied composition for the treatment of osteolysis of the region of bone around a metal object in or contacting the bone. The metal object is usually a screw or pin which has been inserted in bone to hold a fracture, non-union or break together. Treatment includes injecting at least one dosage of the injectable liquefied composition of this invention, which comprises a non-necrotic vascular sclerosing fatty acid compound and a liquid carrier, into the ossifluent region around the metal object. The result is a substantially complete curing (return to normal, healthy bone) of the ossifluent region.

One embodiment of this invention involves the treatment and healing of "the dry socket syndrome", which is localized osteomyelitis of the alveolar crypt in the maxilla and/or the mandible. This is done by the use of one of the compositions of this invention containing a non-necrotic vascular sclerosing fatty acid compound.

Perhaps more importantly, this invention involves the prevention of "the dry socket syndrome". The prevention can be carried out by placing a composition containing a non-necrotic vascular sclerosing fatty acid compound directly into the extraction site immediately following extraction of the tooth.

The (injectable) liquefied compositions described herein can be used, but preferably the creams described herein are used. Even more preferably, a non-water-soluble or non-water-miscible cream base is used in the cream or as a protective cover for the water-miscible or water-soluble cream. Any suitable non-water-soluble or non-water-miscible cream base can be used, but the preferred one is a mixture of petroleum and lanolin—such cream bases are described in more detail below.

A dry socket is a condition which occurs after tooth extraction, resulting in exposure of bone with localized osteomyelitis of an alveolar crypt, and symptoms of severe pain. Osteomyelitis is inflammation of bone caused by a pyogenic organism. It may remain localized or it may spread through the bone to involve the marrow cortex, cancellous tissue and periosteum.

Inasmuch as the actual pulling and tearing mechanism employed during extraction dictates that minute fragmenting of the periosteum and bone must occur, applicant can then postulate that the same pathological changes follow as do show a fracture, per se, occurs. At this tramatic time some cells are completely destroyed - others are damaged. When part of a cell is damaged, transmembrane resting potential at this area may be zero and permeability to ions may be very high. It has been said that perhaps the remaining part of the cells, with raised metabolic activity, can continue to sustain ionic separations despite the loss through the injured area. This cellular area condition, rather it be completely destroyed or moderately damaged, would produce an injury current (pain). The direction of the current is such that the damaged area appears as a source of negative charge. The violent pull at the time of extraction would tend to create some hematomas, clots and a "broken field" (bioelectric) current flow. Such alteration could then become a cesspool whereby the pyogenic organism could readily function osteomyelitis). By applying a composition containing as non-necrotic vascular sclerosing fatty acid compound directly following extraction, the following will occur: (1) clots, per se, will not form in such concentrated bioelectrical fields; (2) the electrical current flow could be more stabilized; and (3) a more stabilized pH. This major stabilizing at the time of trauma has a tendency to produce a more ideal field, for an osteogenic conversion of selected cell function—thus sealing the cavity and lessening the changes of the seating of pyogenic organisms.

"The dry socket syndrome" is very much the same condition which, for example, would occur during surgery of the caprus. A different bone and a different initial exposure (pulling or tearing is opposed to cutting) is involved, but the fact remains that the ensuing cellular changes remain pretty much the same.

Another embodiment of this invention involves the use of a liquefied composition comprised of a non-necrotic vascular sclerosing fatty acid compound and a liquid carrier or a cream containing a non-necrotic vascular sclerosing fatty acid compound and a carrier for the treatment of bone, including the periosteum which has been out, or otherwise penetrated during open reduction surgery. After the surgery, the material containing the non-necrotic vascular sclerosing fatty acid compound is applied to the bone area which is cut or the like. (This should be done even if no visible cuts or the like are seen, as mosaic cuts or the like may be present.) A rapid healing of the bone cut or like occurs, faster than if the bone cut or like was not treated (left to natural healing). The use of the compositions of this invention lessens infection at the time of the "open reduction" surgery—see the above discussion of "the dry socket syndrome".

If a liquefied composition (using say a water carrier) is used, it can be used as a foam or a spray.

The term liquefied composition includes a cream.

A cream is preferred in some instances, and a thioxtropic gel is most preferred. Faster curing is believed to occur when a cream is used. A cream has a number of advantages and disadvantages which have been discussed above.

This embodiment also applies to open reduction of a fractured bone. The above discussion applies to this feature of this embodiment.

The (injectable) liquefied compositions described herein can be used, but preferably the creams described herein are used. Even more preferably, a non-water-soluble or non-water-miscible cream base is used in the cream or as a protective cover for the water-miscible or water-soluble cream.

Another embodiment of this invention is a process for the treatment of the synovial fluid, in a region between two bone surfaces which are in juxtaposition which has become polarized. The process involves applying at least one dosage of a liquefied composition comprised of a buffer and a fat solvent having a high dielectric constant onto the skil adjacent to said two bone surfaces. The preferred fat solvent is dimethyl sulfoxide and the composition can contain a non-necrotic vascular sclerosing fatty acid compound.

After, before or along with the treatment of the demineralized region around the screws, pins, etc., with the vascular sclerosing anionic agent, the bone fracture, break or nonunions of the man or the animal can be treated. Preferably this additional treatment is conducted only after the screws etc., have been removed. This additional treatment includes: aligning (only when necessary) the bone parts for setting; and then injecting at least one dosage of the injectable liquefied composition of this invention, which is comprised of a non-necrotic vascular sclerosing fatty acid compound and a liquid carrier, into the site of the fracture, break or nonunion area of the bone until there is a substantially complete bone union. This additional treatment is described in detail elsewhere herein. Preferably another dosage is injected a week or two after the first dosage and then every week or two thereafter, as needed, until there is a substantially complete bone union. Preferably each dosage of the injectable liquefied composition is injected into the site of the fracture, break or nonunion at its axis. By injecting a non-necrotic vascular sclerosing fatty acid compound at the axis of the fracture "struts" are chemically introduced, giving rise to sheer and thus alignment. The lack of the cast not only eliminates atrophy of muscles and the complication of "lipping", but the movement of bone against the tension of muscle insertion helps to promote the flow of blood to and from the damage area.

This invention can be used to treat man and/or animal. This invention is particularly useful in the treatment of racing and troting horses; can be used to treat, for example, all equine, e.g., horses and mules, donkeys, sheep, goats, swine, bovines, e.g., oxen and cows, dogs, poultry, cats, etc.

After treatment using the injectable liquefied composition of this invention and healing of bone breaks, fractures and non-unions of racing horses, no lameness due to re-fracturing, etc., has been noted even after a large number of races.

DETAILED DESCRIPTION OF THIS INVENTION

Figure 1:
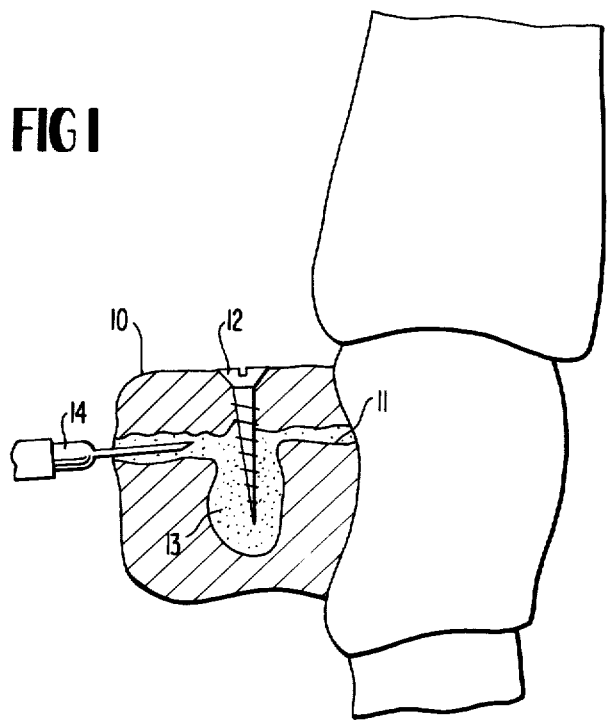

In FIG. 1, the bone is located at 10, the locus of the fracture being indicated at 11. Screw 12 holds the fracture together. The demineralized or ossifluent region around screw 12 is indicated by 13. 14 is an exploratory hypodermic needle which is inserted into the demineralized region 13. The injection is made through needle 14.

Figure 2:
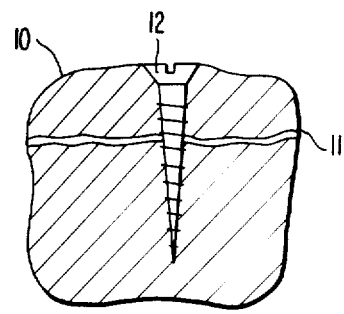

In FIG. 2, demineralized region 13 is absent around screw 13.

Figure 3:
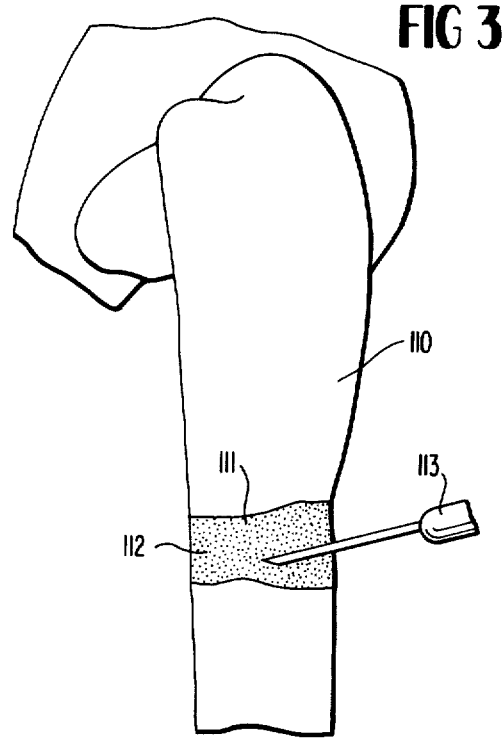

In FIG. 3, the bone is illustrated at 110, the locus of the fracture being indicated at 111 and a blood clot 112 (hematoma in periosteum). 113 is an exploratory hypodermic needle which is inserted into the axis of fracture site 111. The injection is made through needle 113.

Figure 4:
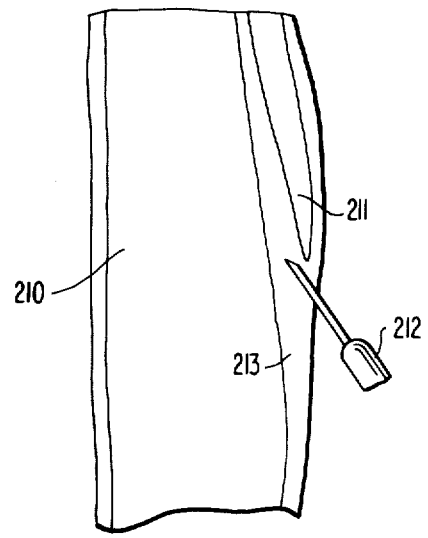

In FIG. 4, the main bone is illustrated at 210, the minor bone is illustrated at 211, and the interface region of bones 210 and 211 is illustrated at 212. 213 is an exploratory hypodermic needle which is inserted into interface region 212. The injection is made through needle 213.

As used herein the phrase "alien material" means metals or other substances which cause the osteolysis demineralization of the bone. Examples of such metals are iron, steel, ferrous alloys, copper alloys, aluminum, aluminum alloys, etc. The phrase "metal object" includes any object such as a screw which is metallic, and is in or contacts the bone. The metal object can be clad or coated with other substances such as chrome or stainless steels. Examples of other substances are rigid resinous materials.

The alien materials can be in the form of screws, pins, and so forth inserted in the bone in order to hold together a fractured bone or merely inserted in the bone for some other purpose (for example as electrodes). The alien material can also be in any other form, such as, a plate attached to or in contact with the bone (for example, as a plate screwed to two vertebra where an intermediate vertebra has been removed).

As used herein the term mosaic fracture includes minute apophysis fractures, minute smear fractures and micro-stress fractures or lesions.

The term liquefied composition includes slurries, suspensions, solutions, etc.

All of the components of the liquefied composition must be and are substantially non-toxic in the amounts under the conditions of use.

The pH of the liquefied composition should be between about 8 and about 11, and preferably between about 9 and about 10. Each non-necrotic vascular sclerosing fatty acid compound will produce a different pH at a different concentration levels, so non-toxic agents may be added to adjust the pH level, e.g., sodium dihydrogen phosphate or sodium hydroxide, can be used when sodium oleate or another non-necrotic vascular sclerosing fatty acid compound is used.

It should be noted that alkali metal salts of fatty acids in general have an alkaline or neutral pH. Examples are: sodium oleate, alkaline pH; potassium acetate, pH of 9.7 (0.1 M); potassium stearate, strongly alkaline pH; sodium stearate, strongly alkaline pH; lithium formate, practically neutral pH; potassium formate, practically neutral pH; sodium acetate, pH of 8.9 (0.1 M); sodium propionate, slightly alkaline pH; sodium morrhuate, alkaline pH; lithium acetate, neutral pH; sodium formate, neutral pH; sodium phylliate, pH of 8.7 to 9.2; and sodium ricinoleate, alkaline pH. The above is usually due to hydrolysis in the aqueous solution.

The most preferred unsatuarated fatty acids have eighteen carbon atoms, and one double bond usually is at the middle of the chain. The most preferred of such fatty acids is oleic acid (i.e., cis-9-oleic acid or cis-9-octadecenoic acid). The next preferred of such fatty acids is elaidic acid (i.e., trans-9-octadecenoic acid). Examples of other unsatured fatty acids having one double bond (i.e., monoethenoid fatty acids) having eighteen carbon atoms are: 2-octadecenoic acid (cis and trans forms), $CH_3(CH_2)_{14}CH=CHCOOH$; 3-ocadecenoic acid, $CH_3(CH_2)_{13}CH=CHCH_2COOH$; 4-octadecenoic acid, $CH_3(CH_2)_{12}CH=CH(CH_2)_2COOH$ 5-octadecenoic acid, $CH_3(CH_2)_{11}CH=CH(CH_2)_3COOH$; 6-octadecenoic acid (cis and trans forms) $CH_3(CH_2)_{10}CH=CH(CH_2)_4COOH$; 7-octadecenoic acid (cis and trans forms), $CH_3(CH_2)_9CH=CH(CH_2)_5COOH$; 8-octadecenoic acid (cis and trans forms), 10-octadecenoic acid, (cis and trans form), $CH_3(CH_2)_6CH=CH(CH_2)_8COOH$; 11-octadecenoic acid (cis and trans form), $CH_3(CH_2)_5CH=CH(CH_2)_9COOH$; 12-octadecenoic acid (cis and trans forms), $CH_3(CH_2)_4CH=CH(CH_2)_{10}COOH$; 15-octadecenoic acid (trans form), $CH_3CH_2CH=CH(CH_2)_{13}COOH$; 16-octadecenoic acid (trans form), $CH_3CH=CH(CH_2)_{13}CH_2COOH$; and 17-octadecenoic acid $CH_2=CH(CH_2)_{14}CH_2COOH$. It is believed that the fatty acids having the unsaturation at one end of the hydrocarbon chain may have undesirable properties and effects in the processes of this invention, i.e., slower healing, less complete healing and the like - such compounds are useful, but less preferred in result.

Examples of other useful monoethenoid fatty acids are: 2-tridecenoic acid; 11-tridecenoic acid; 12-tridecenoic acid; 2-dodecenoic acid; 5-dodecenoic acid; 6-dodecenoic acid; 7-dodecenoic acid; 9-dodecenoic acid; 10-dodecenoic acid; 11-dodecenoic acid; 9-eicosenoic acid, $CH_3(CH_2)_9CH=CH(CH_2)_7COOH$; 11-eicosenoic acid; 14-eicosenoic acid; 2-undecenoic acid; 6-undecenoic acid; 9-undecenoic acid; 10-undecenoic acid; 2-decenoic acid; 3-decenoic acid; 4-decenoic acid; 8-decenoic acid; 9-decenoic acid; acrylic acid, $CH_2=CHCOOH$; β-methylacrylic acid (cis and trans forms), $CH_3CH=CHCOOH$; α-methylacrylic acid, $CH_2=C(CH_3)COOH$; vinyl acetic acid, $CH_2=CHCH_2COOH$; β,β-dimethylacrylic acid, $(CH_3)_2C=CHCOOH$; β-pentenoic acid, $CH_3CH=CHCH_2COOH$; allylacetic acid, $CH_2=CHCH_2CH_2COOH$; angelic acid, $CH_3CH=C(CH_3)COOH$ (cis form); tiglic acid, $CH_3CH=C(CH_3)COOH$ (trans form); 2-heptadecenoic acid, $CH_3(CH_2)_{12}CH_2CH=CHCOOH$; 9-heptadecenoic acid (cis and trans forms), $CH_3(CH_2)_6CH=CH(CH_2)_7COOH$; 2-hexadecenoic acid, $CH_3(CH_2)_{12}CH=CHCOOH$; 9-hexadecenoic acid (cis form); 2-tetradecenoic acid; 4-tetradecenoic acid; 5-tetradecenoic acid; 8-tetradecenoic acid; 9-tetradecenoic acid; 2-nonenoic acid; 3-nonenoic acid; 8-nonenoic acid; 2-octenoic acid; 3-octenoic acid; 7-octenoic acid; 2-heptenoic acid; 3-heptenoic acid; 4-heptenoic acid; 5-heptenoic acid; 6-heptenoic acid; 2-hexenoic acid; 3-hexenoic acid; 4-hexenoic acid; 5-hexenoic acid; 15-tetracosenoic acid; 17-hexacosenic acid; and 21-triacentenoic acid.

Examples of fatty acids having a triple bond are: 2-nonynoic acid, $CH_3(CH_2)_5C\equiv CCOOH$; 3-nonynoic acid; 4-nonynoicacid; 5-nonynoic acid; 6-nonynoic acid; 7-nonynoic acid; and 8-nonynoic acid.

Examples of diethenoid fatty acids having eighteen carbon atoms are: 6:8-octadecadienoic acid, $CH_3(CH_2)_8CH=CHCH=CH(CH_2)_4COOH$; 8:10-octadecadienoic acid, (8-trans and 10-trans forms); 8:11-octadecadienoic acid, (8-cis and 11-cis forms); 9:11-octadecadienoic acid, (9-cis and 11-cis and 11-trans forms); 5:12-octadecadienoic acid, (5-cis, 5-trans, 12- trans and 12-cis forms); 9:12-octadecadienoic acid, (9-cis, 9-trans, 12-trans and 12-cis forms); 10:12-octadecadienoic acid, (10-cis, 10-trans, 12-cis and 12-trans forms); 10:13-octadecadienoic acid, (10-cis and 13-cis forms); and 11:14-octadecadienoic acid, (11-cis and 14-cis forms).

Examples of other useful diethenoid acids are β-vinylacrylic acid, $CH_2=CHCH=CHCOOH$; sorbic acid, $CH_3CH=CHCH=CHCOOH$; and geranic acid, $(CH_3)_2C=CH(CH_2)_2C(CH_3)=CHCOOH$.

Examples of tetra-triethenoid fatty acid having eighteen carbon atoms are: 9:11:13:15-octadecatetraenoic acid, $CH_3CH_2(CH_2=CH_2)_4(CH_2)_7COOH$; 6:9:12:15-octadecatetraenoic acid; 5:9:12-octadecatrienoic acid (5-trans, 9-cis and 12-cis forms); $CH_3(CH_2)_4CH=CHCH_2CH=CH(CH_2)_2CH=CH(CH_2)_3COOH$; 6:9:12-octadecatrienoic acid; 6:10:14-octadecatrienoic acid; 8:10:12-octadecatrienoic acid (8-cis, 10-trans and 12 cis forms); 9:11:13-octadecatrienoic acid (9-cis, 11-trans and 13 trans forms); 9:12:15-octadecatrienoic acid (9-cis, 9-trans, 12-cis, 12-trans, 15-cis and 15-trans forms); and 10:12:14-octadecatrienoic acid (10-trans, 12-trans and 14-trans forms).

An example of a useful triethenoid fatty acid is dehydrogeranic acid, $(CH_3)_2C=CHCH=CHC)CH_3)=CHCOOH$.

Examples of fatty acids having four double bonds are clupandoic acid, moroctic acid, arachidonic acid, α-parinaric acid, and β-parinaric acid.

The useful unsaturated fatty acids can contain between 1 and 50 carbon atoms and preferably between 14 and 22 carbon atoms.

Examples of useful unsaturated fatty acids are oleic acid, linoleic acid, licanic acid, eleostearic acid, ricinoleic acid, clupanodonic acid and palmitoleic acid. The useful unsaturated fatty acids can be those containing one double bond, e.g., oleic acid, two double bonds, e.g., linoleic acid, three double bonds, e.g., eleostearic acid, etc.

Saturated fatty acid compounds are useful, but are not preferred. Saturated fatty acid compounds are believed to operate via a different mechanism that unsaturated fatty acids. Saturated fatty acid compounds are slower in bringing about healing and may have undesirable side effects. The useful saturated fatty acids are represented by the general formula: RCOOH, where R can be H, an alkyl group, branched or straight chain. Such alkyl groups should contain between 1 and 50 carbon atoms and preferably between 14 and 22 carbon atoms. Examples of useful saturated fatty acids are formic acid, acetic acid, propionic acid, n-butyric acid, isobutyric acid, n-valeric acid, n-caproic acid, n-heptoic acid, caprylic acid, n-nonylic acid, capric acid, undecylic acid, lauric acid, tridecyl acid, myristic acid, pentadecylic acid, palmitic acid, margaric acid, stearic acid, nonadecanoic acid, heneiscosanoic acid, triosanic acid, lignoceric acid, pentacosanoic acid, cerotic acid, arachidic acid and behenic acid.

Natural or synthetic fatty acids can be used to form the fatty acid compound. Mixtures of fatty acids can be used to form the fatty acid compound. Mixtures of fatty acids can be used, but preferably only mixtures of only unsaturated fatty acid are used. Sodium morrhuate is a mixture of the sodium salts of unsaturated and saturated fatty acids of cod liver oil. Undesirable results and slower healing rates are obtained when sodium morrhuate (or unsaturated fatty acid compounds) is used.

Useful fatty acids for forming the fatty acid salts which contain one or more hydroxyl groups are, e.g., dihydroxystearic acid and ricinoleic acid. Useful hydrogenated fatty acids are cod liver oil, fatty acids, tallow fat fatty acids, castor oil fatty acids, rape oil fatty acids, peanut oil fatty acids, linseed oil fatty acids, tung oil fatty acids, oiticia oil fatty acids, lard oil fatty acids, neat's foot oil fatty acids, whale oil fatty acids, olive oil fatty acids, coconut fat fatty acids, palm fat fatty acids, butter fat fatty acids, lard fat fatty acids, palm fat fatty acids, butter fat fatty acids, and fish oil fatty acids. The useful hydrogenated fatty acids can be obtained from vegetable oils and fats, and animal oils and fats. Polymeric fatty acids can be used.

A fatty acid soap like monoethanolamine oleate is preferred when the fracture and particularly a open reduction surgery site is treated immediately thereafter. When a fracture is treated 24 to 36 hours or longer after the occurrence of the fracture, sodium oleate is preferred. In the cause of the delay often occurring in the treatment of fractures, things such as the sodium and potassium balance are then out of phase.

The most preferred fatty acid compounds are soaps such as the reaction product of fatty acids and organic bases, e.g., methylamine, triethanolamine, monoethanolamine, diethanolamine, phenyl ethanol amine, ephedrine and pseudoephedrine. Fatty acid soaps of mono- di- and tri-alkyl amines and aryl amines can be used. One reason for this is due to the present of the organic base moiety, which makes the fatty acid compound more psychologically compatible. Such compounds give very fast healing. The fatty acid compounds can be esterified fatty acids, e.g., methyl formate, ethyl propionate and n-amyl acetate. Such are advantageous because the compounds are almost entirely organic. The fatty acid compound can be a fatty acid salt, also a most preferred class. The fatty acid salts can be those prepared from metals, such as, aluminum and alkaline earth metals, e.g., calcium, but are preferably those prepared by alkali metals, e.g., sodium (preferred), lithium potassium, caesium and rubidium. (Ionic fatty acid compounds of sodium such as, sodium oleate, are preferred, even though the potassium salts are usually more soluble. Also, when the sodium belance becomes a factor, the sodium salts are the most preferred.) The metals are used as hydroxides, carbonates, etc. The fatty acid salts can be prepared from ammonia and similar non-metallic inorganic bases.

The most preferred compounds are monoethanolamine oleate and sodium oleate.

Examples of useful compounds of oleic acid are: the methyl ester of cis-9-octadecenoic acid; ethyl ester of cis-9-octadecenoic acid; propyl ester of cis-9-octadecenoic acid; isopropyl ester of cis-9-octadecenoic acid; butyl ester of cis-9-octadecenoic acid; isobutyl ester of cis-9-octadecenoic acid; tert.-butyl ester of cis-9-octadecenoic acid; 3-methylbutyl ester of cis-9-octadecenoic acid; 2-methyl-2-butyl ester of cis-9-octadecenoic acid; phenyl ester of cis-9-octadecenoic acid; m-tolyl ester of cis-9-octadecenoic acid; p-phenylphenacyl ester of cis-9-octadecenoic acid; and the amide ester of cis-9-octadecenoic acid.

Examples of useful compounds of elaidic acid are: the methyl ester of trans-9-octadecenoic acid; the ethyl ester of trans-9-octadecenoic acid; and the amide ester of trans-9-octadecenoic acid.

Examples of useful octadecenoic acid compounds are: the methyl ester of trans-2-octadecenoic acid; the ethyl ester of trans-2-octadecenoic acid; the amide ester of trans-2-octadecenoic acid; the methyl ester of trans-3-octadecenoic acid; the methyl ester of cis-6-octadecenoic acid; the p-bromophenacyl ester of cis-6-octadecenoic acid; the amide of cis-6-octadecenoic acid; the triglyceride of cis-6-octadecenoic acid; the ethyl ester of trans-10-octadecenoic acid; the amide ester of trans-10-octadecenoic acid; the p-bromophenacyl ester of cis-11-octadecenoic acid; the methyl ester of trans-11-octadecenoic acid; the ethyl ester of cis-12-octadecenoic acid; and the methyl ester of trans-16-octadecenoic acid.

Examples of other useful monoethenoid fatty acid compounds are: the lithium salt of 9-heptadecenoic acid; the amide of 2-heptadecenoic acid; the methyl ester of 9-heptadecenoic acid; the ethyl ester of 9-heptadecenoic acid; the ethyl ester of 2-hexadecenoic acid; the methyl ester of 9-hexa decenoic acid; the ethyl ester of 9-hexadecenoic acid, the ethyl ester of 2-tetradecenoic acid; the methyl ester of 4-tetradecenoic acid; the ethyl ester of 4-tetradecenoic acid; the methyl ester of 9-tetradecenoic acid; the amide ester of 2-tridecenoic acid; the methyl ester of 12-tridecenoic acid; the ethyl ester of 12-tridecenoic acid; the amide of 7-doodecenoic acid; the ethyl ester of 11-doodecenoic acid; the methyl ester of 11-doodecenoic acid; the amide of 9-eicosenoic acid; the ethyl ester of 9-eicosenoic acid; the methyl ester of 11-eicosenoic acid, the amide of 2-undecenoic acid; the amide of 6-undecenoic acid; the ethyl ester of 9-undecenoic acid; the copper salt of 10-undecenoic acid; the ethyl ester of 10-undecenoic acid; the amide of 10-undecenoic acid; the amide of 2-decenoic acid; the methyl ester of 8-decenoic acid; the ethyl ester of 2-nonenoic acid; the ethyl ester of 8-nonenoic acid; the ethyl ester of 7-octenoic acid; the methyl ester of 7-octenoic acid; the amide of 2-octenoic acid; the methyl ester of 4-heptenoic acid; the methyl ester of 2-hexenoic acid; the ethyl ester of 2-hexenoic acid; the amide of 3-hexenoic acid; the methyl ester of 5-hexenoic acid; the ethyl ester of 2-pentenoic acid; and the amide of 15-tetracosenoic acid.

Examples of useful diethenoid fatty acid compounds having eighteen carbon atoms are: the methyl ester of 6:8-octadecadienoic acid; the methyl ester of 9:11-octadecadienoic acid; the ethyl ester of 9:11-octadecadienoic acid; the sodium salt of 9:12-octadecadienoic acid; the methyl ester of 9:12-octadecadienoic acid; the ethyl ester of 9:12-octadecadienoic acid; the amide of 9:12-octadecadienoic acid; the benzyl amide of 9:12-octadecadienoic acid; and the methyl ester of 10:12-octadecadienoic acid.

Examples of useful triethenoid fatty acid compounds having eighteen carbon atoms are: the methyl ester of 6:10:14-octadecatrienoic acid; the methyl ester of 9:11:13-octadecatrienoic acid; the ethyl ester of 9:11:13-octadecatrienoic acid; the methyl ester of 9:12:15-octadecatrienoic acid; the ethyl ester of 9:12:15-octadecatrienoic acid; and the methyl ester of 10:12:14-octadecatrienoic acid.

Examples of useful triple bond fatty acid compounds are: the methyl ester of 2-nonynoic acid; the methyl ester of 4-nonynoic acid; the methyl ester of 5-nonynoic acid; the methyl ester of 6-nonynoic; the methyl ester of 7-nonynoic acid; the methyl ester of 8-nonynoic acid; the amide of 2-nonynoic acid; the amide of 3-nonynoic acid; the amide of 4-nonynoic acid; the amide of 5-nonynoic acid; the methyl ester of 6-nonynoic acid; the amide of 7-nonynoic acid; and the amide of 8-nonynoic acid.

Examples of specific useful compounds of fatty acids which can be used as non-necrotic fatty acid compounds are: sodium oleate; sodium psylliate (a mixture of the sodium salts of psyllium oil liquid fatty acids); sodium ricinoletae; ethylamine oleate; monoethanolamine oleate; sodium formate; sodium acetate; and calcium propionate. Salts of fatty acids are quite useful, particularly those formed from alkali metals.

The liquified solution should contain between about 0.5 and about 10 percent by weight of the fatty acid compound, and preferably contain between about 1 and about 5 percent by weight of the fatty acid compound.

Examples of the liquid carrier for the non-necrotic fatty acid compounds are water, monoglycerides, diglycerides, etc. A mixture of water and ethanol is the preferred liquid carrier; salt (NaCl) can be added to make an isotonic aqueous solution as the liquid carrier.

The useful vascular sclerosing fatty acid compounds must be non-necrotic in effect or operation and must not cause the pathologic death of none or more cells, or a portion of tissue or organ, resulting from irreversible damage to the necleus.

Anodynes in amounts of up to and including about 5 percent by weight may be added. An anodyne is an agent which has the power to relieve pain. An example of a useful anodyne is benzyl alcohol. In general small amount of antiseptics or anaesthetics can be used.

Suitable preservations can be added in an amount not to exceed 0.5 by weight.

Up to about 5 weight percent, based on the weight of the total composition, of mild anesthetics and/or antiseptics can be added. Examples of such materials are chlorobutanol and benzyl alcohol.

The injectable liquefied composition preferably contains a buffering agent, such as, sodium phosphate such as secondary sodium phosphate, sodium carbonate, or the salt of a weak organic acid with a strong base of which sodium citrate is an example. Examples of useful buffers are disodium hydrogen phosphate and sodium dihydrogen phosphate (preferred).

Each dosage preferably contains between 0.1 and 10 c.c., depending on the size, etc., of the man or animal and the bone being treated. More preferably, the dosage usually contains between 0.2 and 5 c.c. When a horse is being treated, the best results are obtained when the dosage is between 0.5 and 3 c.c.

The dosage used in treating bucked shins preferably ranges from 1 to 25 c.c., most preferably 5 to 12 c.c. Treatment of other types of mosaic fractures use amounts that are relative to the size of the fracture area, using the data herein for bucked shins. A series of ⅛ to ¼ cc are made around the periphery and in the middle regions of the bucked shins or splints. This means that about 30 to 40 small injections are made, preferably in three lines running the length of the afflicted region (one on each side and one down the middle). A large injection of 1 cc or more is not as effective as a number of smaller injections due to the fact that a large mosaic fracture area has to be covered. Such a large injection also forms a lump that takes awhile to dissipate since most of such an injection has not actually been placed at the fracture site and a fatty acid compound is usually not very soluble in body fluid (materials such as ethanol are often used in small amounts to aid in the solubility factor in formulating the dosage).

In the preferred compositions using sodium oleate, the ethanol and/or phosphate buffer are believed to aid and complement the action of the sodium oleate in a slightly synergistic manner.

A sclerosing agent is generally defined as an agent which causes an induration produced in an organ by increase of its interstitial connective tissue. There are two types of sclerosing agents, although one usually works to a certain degree in the other field. The most widely known are the vascular sclerosing agents which are used in soft tissue. The bone field also uses the term sclerosing agent to mean anything (including heat) which aids (new) bone growth. Since applicant is using chemical sclerosing agents in the bone field, applicant uses the term vascular sclerosing agent or compound to use a more well known term to help identify what type of action the agent or compound has or produces. (To point out why this terminology has to be used, applicant points out that the term osteosclerosis has a specific meaning which applies to abnormal hardness and density of bone.)

A sclerosing agent in soft tissue is a chemical irritant. Sodium oleate, in that sense of the word, is weak sclerosing agent. In the bone art, where sclerosing agent means a factor which aids in healing, sodium oleate is an excellent sclerosing agent. To specify this the applicant has used the term vascular sclerosing agent because it is art known, but is used in the sense that it signifies a certain type of agent which achieve or aids in bone healing. More correctly the term might be merely sclerosing agent, but the other term has the same meaning herein, i.e., aids or achieves bone healing.

Sclerotherapy is the injecting of sclerosing solutions, so the use of injectable solutions in this invention might be termed osteo-sclerotherapy.

The oleates are weak sclerosing agents in soft tissue (little alteration of soft tissue), and are excellent sclerosing agents in bone (altering by way of osteolysis or osteogenesis). Salts like sodium and potassium oleate are excellent sclerosing agents in bone. Monoethanolamine oleate is also an excellent sclerosing agent in bone (as are all hydroxy amine oleates). The latter has the advantages of not being as hydrophilic as the sodium and potassium salts, is very useful in a thixotropic gel, is organic and not highly ionic and its hydroyl group gives it some polarity. The oleates and other unsaturated fatty acid cause immediate stimulation of the osteoblasts and bone growth. Compounds such as sodium morrhuate first cause an infiltration of soft tissue into the fracture site (causing healing problems) and then cause stimulation of the osteoblasts and bone growth (with much poorer healing occurring). Sodium morrhuate is a sodium salt of saturated and unsaturated fatty acids of cod liver oil—the saturated fatty acid compounds allow soft tissue infiltration before the osteoblasts are stimulated.

A quite unexpected advantage of the non-necrotic vascular sclerosing agents is that they stimulate bone growth only to the degree needed to achieve the healing. Sodium oleate is best in this aspect (with sodium morrhuate often causing a slight overgrowth lipping the fracture site).

The no n-necrotic vascular sclerosing fatty acid compounds appear to have a hormone-like activity in the bone healing process. The term hormone has been applied to a chemical substance (not produced by special glands) which have a specific effect on the activity of a certain organ. Applicant theorizes that the agents of applicant's inventions act in a similar manner on the bone healing process. The compounds formed from an unsaturated fatty acid having one double bond particularly are effective, apparently, in acting as messengers (synthetic and externally introduced) that sort out the osteoblasts and trigger them into new bone growth. This is why the compounds of this invention can be viewed, on one sense, as hormone-like. The compounds of this invention may be hormonal (pertaining to or of the nature of hormones), or may be hormonagogues (agents that stimulate the productions of hormones in this case ones that stimulate bone growth) or may be hormonopoietic (pertaining to, characterized by or stimulating hormonopoiesis, which is the production of hormones, in this case ones which stimulate bone growth). Or the compounds of this invention may be in effect cause the production of local repair hormones which would be locally produced substances with hormone-like properties which stimulate bone growth. The above is only theory. An apt term for the compounds of this invention might be osteogenesis -stimulating aftificial hormones.

As used herein the term gel or cream includes gel, ointment, cream and the like. Creams or gels are used herein as a separate category and as a class of liquefied compositions.

One advantage of the use of a gel is that such minimizes the stability problems by suspending the chemical action. The gel increases the shelf life of, for example, sodium oleate by slowing down the hydrolysis thereof.

(When some gel bases are used, some water may have to be used in the gels to get the proper consistency.)

The cream carrier, vehicle or base (which is used in topical gels) can be any suitable carrier or base material which forms a paste or the like. Useful gel carriers can be: methyl-cellulose; modified starches (5 to 40 percent by weight based on the total gel weight); polyvinyl alcohol (up to 7 percent by weight based on the total gel weight); gelatin (5 to 30 percent by weight based on the total gel weight); Carbowax; hydroxymethyl cellulose or hydroxyethyl cellulose or hydroxypropyl cellulose or methyl cellulose (2 to 20 percent by weight based on the total gel weight); metallic salts of fatty acids (15 percent and above produces a gel); fatty acid esters (e.g., propylene glycol ethers of oleic acids); a water-miscible base made from propylene glycol, stearic acid, diglycol stearate and triethanolamine; glycerin and polyethylene glycol; water-dispersible petroleum base containing octylphenoxyethanol; polyethylene glycol; water miscible base compound of propylene glycol monostearate, isopropyl myristate, propylene glycol, stearic acid, sorbitol, water and polyoxyethylene sorbitan monopalmitate; polyethylene glycols and propylene glycol cetyl alcohol, stearyl alcohol, spermacetic; polyoxyl 40 sterate, polyoxyl 8 stearate, water and glycerin; glycerin, cetyl alcohol, mineral oil, an ethoxylated fatty alcohol, water, methylparaben and propylparaben. Such gels keep the active ingredient at the site where topically applied.

Injectable gels should be thixotropic gels. This allows the gel to stay in place once injected into the fracture site and to have the property of easily being injectable. Useful gel carriers or bases which form thixotropic gels can be: sodium carboxymethylcellulose (0.5 to 25 percent by weight based on the total gel weight); and polyvinyl propylene (Pasdone C, made by GAF) (1 to 30 percent by weight based on the total gel weight. To form thixotropic gel, the art knows that certain concentrates of the gel base having a particular viscosity property or molecular weight need be used. The injectable gel represents a preferred embodiment of this invention. This invention also includes a pre-filled hypodermic containing an injectable thixotropic gel of this invention—this is a preferred embodiment of this invention.

In general, the gel carrier should be non-drying and water-miscible or water-soluble. The gel carrier can be an emulsifier. The gel carrier should be odorless, non-irritating and non-toxic. The gel carrier can be colorless or colored.

The gel can be used in suppository form or the like where it is necessary to leave the incisure or cut open (or to reopen periodically). Such suppository-like units can contain a cream, for example, made from lactose, polyethylene glycol 400, polysorbate 80, polyethylene glycol 4000 and glycerin, or which is a water-soluble base of polyethylene glycol and polyoxyethylene palmitate, or which is cocoa butter.

The gel can be applied as an aerosal spray. The basic gel carrier could be isopropyl myristate with an inert propellant mixture of trichloromonfluoromethane and dichlorodifluoromethane.

The gel can be applied as a foam. A suitable water-miscible foaming agent can be used.

In certain instances, for example, in the treatment of "dry sockets", it is desirable to use a cream or gel which comes in contact with moving body fluids or outside fluids or solids (such as, water and food). Such gel bases generally should be non-drying, should not disintegrate or liquefy at body temperature and should not be washed away by things such as mouth fluids. Such gel bases should not be water-miscible or water-soluble. These cream bases can be used as protective layers for the water-miscible or water-soluble creams of this invention. An example of a non-water soluble gel base is a mixture of petroleum and lanolin.

In one study, four holes were drilled through the cortex of the tibias of three mature dogs. Saline solution was placed in one hole in each dog; a gel composed of sodium oleate in a buffered solution of sodium hydroxide (pH 9.8) and methylcellulose was placed in another hole in each leg; the sodium oleate composition without the methylcellulose was placed in the third hole in each dog; and methylcellulose was placed in the fourth hole in each dog. Bone reactions was removed from each hole at one week intervals. The test was conducted for five weeks. The gel produced bone growth more rapidly than the others, followed by good results by the solution of active material, followed by the methylcellulose and then the control saline solution. This study showed the more rapid bone growth using gels and solutions containing sodium oleate.

The following four seats of unsoundness in the equine, plus in other animals and man, namely, ringbone, splints bucked shins and osselets can be successfully treated in much the same manner as a fracture or non-union of a fracture is treated according to this invention. Heretofore these four sets of unsoundness have been erroneously treated. Each of the four unsoundness have been often classified as a form of periostitis and applicant and others skilled in the art know that this is incorrect. These unsoundnesses are in fact examples of periostostetis.

Periostitis is the inflammation of the periosteum. Periostostetis is the inflammation involving both bone and its connective tissue covering (periosteum), or a mosaic fracture of the bone and periosteum.

Ringbone or (phalangeal exostosis) is new bone growth which occurs on the first, second or third phalanges. It is a result of a periostetis and may lead to an osteoarthritis or ankylosis of the pastern or coffin joints. Splints is a disturbance of the fibrous interosseous ligmanet, between the second and third metacarpal bones, or between the third and fourth metacarpal bones, causes splints. This irritation to the periosteum and underlying bone causes periostetis and new bone growth. Bucked shins is a periostetis of the dorsal (anterior) surface of the third metacarpal or third metatarsal bone. Bucked shins result from a tearing of the periosteum along the front of the metacarpal bone. Osselets occur at the fetlocks along the anterior margin of the articular cartilage of the large metacarpal bone. When they appear they are hot, painful, and comparatively soft swellings. Radiographs will show a rarefaction of the bone where the joint capsule is attached. Later, calcium will be deposited and an exostosis will form in this area.

Because of the close connection between the periosteum and the bone itself, it is very difficult to determine whether an ostitis is present, however, the applicant feels it is evident and is displayed clinically through the recurrance of lameness and the continued proliferations which lead to ankylosing.

All four of these ailments are created by a traumatic pulling or tearing of the periosteum. Bio-mechanically it can be demonstrated that it would be quite impossible just to disturb the periosteum per se inasmuch as all areas also involve insertion areas of tendons, upon the bone. In other words, periostitis would manifest itself as an infection of the periosteum via the blood stream whereas periostostetis would be present in a traumatic pulling or tearing. This is demonstrated by the fact that all four ailments eventually lead to bone proliferation. Osteocytes are the normal bone cells, and are associated with the maintenance of bones as a living tissue. Osteocytes cannot divide or multiply.

Osteoblasts are special cells concerned with the deposition of bone, and are derived from the primitive undifferentiated mesenchymal cells of the reticulum of the bone marrow, the endosteum, the Haversian systems and the osteogenic layer of the periosteum. The primary issue in this hypothesis is the production of osteoblasts produced at the osteogenic layer of the periosteum. If the periosteum was merely inflammed the damaged cells would not be too extensive and therefore ions would be able to flow in and out of the cell through the damaged membrane for a considerable time, and this being the condition, the mechanism of osteoblastic formation would not take place, as it appears that the remaining part of the cell, perhaps with raised metabolic activity, can sustain ionic separations despite the loss through the injured area.

If the periosteum is ripped or torn the cell damage is more extensive. A steady current flow, known as an injury current, is detected near injured tissue. The direction of the current is such that the damaged area appears as a source of negative charges. Should these negative charges diminish one could assume that a state of polarization could occur. Inasmuch as the violent tearing would have produced a hemorrhage one could therefore postulate that the hemorrhagic polarization could be present.

The pickup electrode would occur at the torn areas of the periosteum. The residues from electrode reactions may be too great for them to diffuse away into the solution and may accumulate near the electrodes. If such residues should be hydrogen bubbles, an insulating layer may form around the electrode surface, so that its resistance becomes very high. This reaction is called polarization of the electrodes and can render electrodes unfit for use. The polarized exudate would loose its permeability and thus could not escape. The surrounding blood bessles would become compressed, cutting off fresh blood supply to the surrounding area of bone which in turn would become necrotic. The then minute necrotic areas of bone gradually separate and are zoned off by fibrous tissue and involucrum (a covering or sheath, such as contains the sequestrum of a necrosed bone fragment). The clinical demonstration of proof of this point has been demonstrated a great number of times over the years.

For example, re ringbone, see O. R. Adams, "Lameness in Horses" 2nd Ed., (1967). Applicant has found that if the initial injury is treated as being an minute apophysis fracture and/or minute smear fractures the disease cannot manifest itself into the chronic state. The morbid state is therefore a result of the initial state not being properly treated. Unfortunately, ringbone is produced for the most part by faulty conformation (e.g., toed-in or toed-out) and therefore must be classified as a predisposed bio-mechanical failure. It is for this reason that the applicant is not suggesting a "cure" per se, but has found that if the initial tearing of the periosteum is treated in the same manner a fracture is treated herein, that an arrest of or prevention of further necrosing of bone can be made. It could well prevent the stage of fibrous union which would belie the true fact of soundness. In other words, when proper healing of bone and periosteum is effected by this invention, the chances of diffusion oare greatly reduced, and it is the continued diffusion in ringbone which produces the chronic results, such as, alkylosing, etc.

Concerning osselets, all clinical aspects of osselets are identical to those of ringbone. The only difference is in location. Osselets form along the anterior margin of the articular cartilage of the large metacarpal (cannon bone) whereas ringbone forms on the phalanges. The result proliferation is circulas due to the pull created by the anatomical insertions. The events leading to chronic osselets are identical to those leading to chronic ringbone. The traumatic pull to the bone and its periosteum in both ailments is circumscribed and so is the profile of proliferation. Splints do diffuse and nature's only correction remains in the form of a calcium proliferation (as would occur in the healing of a fracture). It is interesting to note that the profile of proliferation in both ringbone and osselets is circular as opposed to the longitudinal profile of proliferation produced in splints and bucked shins. The profile of proliferation will follow the line of mechanical stress produced upon the bone and its periosteum and insertions. Healing must therefore preclude the change of a fibrous union which would not be adequate enough to prevent diffusement.

The four ailments, ringbone, osselets, splings and bucked shins, all involve the production of osteoblasts acting as a healing or arresting mechanism. Unfortunately, the mechanics of the structures which are governed by conformation can contribute to the continuation of osselets and ringbone. The trauma created by faulty conformation can continue to produce wear and tear on the bones and their articulating surfaces, throughout the life of the animal. The maturity of the periosteal attachments to the bone would not be adequate enough to preclude the traumatic damage of faulty mechanics. It is for this reason that the applicant is not suggesting a "cure" per se, for osselets or ringbone but instead is suggesting that the "green" formations being properly treated in their initial stages could well retard or greatly prolong the chronic changes taking place due to the bio-mechanic failures. Treatment involves injection into the ailment site of the composition of this invention.

Splints can be cured as these involve anatomical structures where the osteogenic production has in essence created "struts" of structural benefit. The fusing of the 3rd metacarpal to the 2nd and/or 4th metacarpal prevents the vertical thrust and torque which precludes the continuation of rupturing of the ligamentous fibers, which are proagated to the periosteum. In truth, a splint which is cured is a blessing in disguise in the young horse. The fusing of these small bones to the principal bone prior to the consequence of normal ossification of their ligament of union (4th year) creates the beneficial rewards of forming a "three-bone-weight-bearing-structure" to better support the carpus. Treatment involves injection into the ailment site using the composition of this invention.

Bucked shins can be cured because this is in essence a condition whereby the osteogenic production acts as a maturity factor in the periosteal attachment to the bone. Bucked shins are rarely seen in adult horses, however, direct trauma to the metacarpal can produce in the adult horse "saucer" fractures. Treatment of both involves injection into the ailment sight using the composition of this invention. The caustic methods of treatment of "bucked shins" which are the first mild cases (which are indeed true cases of periostitis) do little more than to damage the tissues in surrounding areas and in truth weaken their structures. Upon being put back into work the traumatic strain would therefore produce periostostetis and therefore the osteogenic production would ultimately perfect the cure.

The applicant has invented a cure for splints and bucked shins. If treated properly the boney union enhances the structures. Perhaps it is better explained to say that a healed splint (one that cannot diffuse) is an expediency in fusing the small metacarpal to the large (3rd) metacarpal which would occur in the normal ossification of maturity. Bucked shins if treated to heal properly, produce a more solid union of the periosteum and bone and is an "aid" to the young horse lacking such maturity. Microstressfractures must be treated in the same manner as any fracture as the stages of healing are the same, namely, (1) haematoma formation, (2) callus formation, (3) consolidation and (4) remodelling.

In the case of osselets and ringbone, the applicant is disclosing a treatment by which micro-stress-fractures are healed however not a cure because mechanical stress involved in faulty conformation would not be corrected and therefore the healing of the micro-stress-fractures would retard but could not necessarily prevent the traumauc reoccurence.

Unless otherwise stated or indicated, in the following examples, all percentages and proportions are expressed on a weight basis.

The following examples further illustrate, but do not limit this invention.

EXAMPLE 1

An injectable liquefied composition containing 5 weight percent of sodium oleate, 1.5 weight percent of ethanol, enough sodium dihydrogen phosphate to obtain a pH of 9.8 and 50 ml. of sterile distilled water (q.s.). The liquefied composition was placed in several 2 c.c. ampoules. One of the ampoules was used to fill a conventional hypodermic needle syringe. The liquefied solution was injected into the axis or plane of a fresh break of the coffin bone of a horse, the ends being held mutually in alignment during the injection. No cast was used and the horse was not suspended. The treatment was not painful. X-rays indicated that "struts" were produced, giving rise to sheer and thus alignment. The horse was able to "test out" the leg and successfully put minor weight on the foot after about ten days. Another injection was made on the tenth day, and about every ten days thereafter until the fracture was substantially cured after about three months.

EXAMPLE 2

Example 1 was repeated, except that the injectable liquefied composition containing the non-necrotic fatty acid compound of Example 1 was replaced with an injectable liquefied composition comprising an aqueous solution (5 c.c. vial) containing 5 percent of sodium psylliate and 2 percent by weight of benzyl alcohol. That aqueous solution had a pH of 8.9 (enough 10% NaOH solution was added to achieve that level). The fracture was substantially cured in about three months after repeated injections.

EXAMPLE 3

Example 1 was repeated, except that the injectable liquefied composition containing the non-necrotic fatty acid compound of Example 1 was replaced with an injectable liquefied composition comprising an aqueous solution aqueous solution (2 c.c. vial) containing 5 percent of sodium psylliate. A NaOH solution was added to obtain a pH level of 8.7. The fracture was substantially cured in about three months after repeated injections.

EXAMPLE 4

Example 1 was repeated, except that the injectable liquefied composition containing the non-necrotic fatty acid compound of Example 1 was replaced with an injectable liquefied composition comprising an aqueous solution (2 c.c. ampul) containing 5 percent ethylamine oleate and 2 percent benzyl alcohol. The fracture was substantially cured in about three months after repeated injections.

EXAMPLE 5

Example 1 was repeated, except that the injectable liquefied composition containing the non-necrotic fatty acid compound of Example 1 was replaced with an injectable liquefied composition comprising an aqueous solution (2 c.c. ampul) containing 5 percent ethylamine oleate. The fracture was substantially cured in about three months after repeated injections.

EXAMPLE 6

Example 1 was repeated, except that the injectable liquefied composition containing the non-necrotic fatty acid compound of Example 1 was replaced with an injectable liquefied composition containing an aqueous solution (2 c.c. ampul) containing 5 percent of potassium oleate, 3 percent of benzyl alcohol, and enough KOH to bring the pH up to 9.5. The fracture was substantially cured in about three months after repeated injections.

EXAMPLE 7

Example 1 was repeated, except that the injectable liquefied composition containing the non-necrotic fatty acid compound of Example 1 was replaced with an injectable liquefied composition comprising an aqueous solution (2 c.c. vial) containing 2 percent of sodium ricinoleate. That solution has a pH between 8.2 and 8.5. The fracture was substantially cured in about three months after repeated injections.

EXAMPLE 8

Example 1 was repeated, except that the injectable liquefied composition containing the non-necrotic fatty acid compound of Example 1 was replaced with an injectable liquefied composition comprising an aqueous solution (2 c.c.) containing 3 percent sodium oleate. The fracture was substantially cured in about three months after repeated injections.

EXAMPLE 9

Example 1 was repeated, except that the injectable liquefied composition containing the non-necrotic fatty acid compound of Example 1 was replaced with an injectable liquefied composition comprising an aqueous solution (2 c.c. ampul) containing 7 percent of lithium oleate. The fracture was substantially cured in about three months after repeated injections.

EXAMPLE 10

Example 1 was repeated except that the treatment was done to an apex sesamoid fracture of a horse. The fracture was substantially cured in about three months after repeated injections.

EXAMPLE 11

Example 1 was repeated except that the treatment was done to a distal sesamoid fracture of a horse. The fracture was substantially cured in about three months after repeated injections.

EXAMPLE 12

Example 1 was repeated except that the treatment was done to a chip fracture in the carpus of a horse. The fracture was substantially cured in about three months after repeated injections.

EXAMPLE 13

A horse was purchased at the Belmont sale and shipped to West Virginia. X-rays showed a complete transverse fracture of the sesamoid. The horse was shipped to Pennsylvania and confined to a stall for eight months. Then a Stineman pin was inserted to hold the fracture. The Stineman pin was removed after two weeks and a screw was inserted. After 3½ months, healing was occurring at the fracture sight, however, demineralization (osteolysis) had begun around the screw. After six months the horse was sent to a track and put in light training. The horse remained sound for about 25 days and then pulled up lame. An X-ray showed that demineralization had increased (2 months after pulling up lame). The horse was shipped to the applicant's stable and x-rayed; the x-rays showed extensive demineralization around the screw. See FIG. 1. 2 c.c. of an injectable liquefied composition comprising a sterile aqueous solution, containing 5 percent of sodium oleate, 1.5 percent of ethyl alcohol enough sodium dihydrogen phosphate to adjust the pH to 9.8 and 50 ml. of sterile distilled water (q.s.), were injected the same day at one site of the demineralized region around the screw. Seventeen days later 2 c.c. of the sodium oleate solution was injected at one site of the demineralized region. Seven days later 1.5 c.c. of the sodium oleate solution was injected into each of two sites of the demineralized region. Thirty days later, an x-ray was taken of the subject region and the x-ray showed that essentially complete restoration of the demineralization (ossifluent) region to healthy bone had occurred. See FIG. 2.

EXAMPLE 14

Example 13 was repeated, except that the injectable liquefied composition containing the non-necrotic fatty acid compound of Example 13 was replaced with an injectable liquefied composition comprising an aqueous solution (2 c.c. ampoule) containing 5 percent ethylamine oleate and 2 percent benzyl alcohol. The ossifluent region was substantially cured in about two months after repeated injections.

EXAMPLE 15

Example 13 was repeated, except that the injectable liquefied composition containing the non-necrotic fatty acid compound of Example 13 was replaced with an injectable liquefied composition comprising an aqueous solution (5 c.c. vial) containing 5 percent of sodium psylliate and 2 percent of benzyl alcohol. That aqueous solution had a pH of 8.9 (enough NaOH solution was added to achieve that level). The ossifluent region was substantially cured in about two months after repeated injections.

EXAMPLE 16

Example 13 was repeated on a horse having a broken coffin bone. The following procedure was followed to treat the break itself. An injectable liquefied composition comprising a sterile aqueous solution containing 5 weight percent of sodium oleate, 1.5 percent of ethanol and enough sodium dihydrogen phosphate to obtain a pH of 9.8 and the remainder water was placed in several 2 cc. ampoules. One of the ampoules was used to fill a hypodermic needle syringe. The liquefied solution was injected into the axis or plane of the break of the coffin bone of the horse, the ends being head manually in alignment during the injection. See FIG. 3. No cast was used and the horse was not suspended. The treatment was not painful. X-rays indicated that "struts" (of callus along the line of stress) were produced, giving rise to sheer and thus alignment. The horse was able to "test out" the leg and successfully put minor weight in a very short time. Another injection was made on the tenth day, and about every ten days thereafter until the fracture was substantially cured.

EXAMPLE 17

Example 16 was repeated, except that the injectable liquefied composition containing the non-necrotic fatty acid compound of Example 16 was replaced with an injectable liquefied composition comprising an aqueous solution (2 cc. ampoule) containing 5 percentethylamine oleate and 2 percent benzyl alcohol. The fracture was substantially cured in about three months after repeated injections.

EXAMPLE 18

Example 16 was repeated, except that the injectable liquefied composition containing the non-necrotic fatty acid compound of Example 16 was replaced with an injectable liquefied composition comprising an aqueous solution (5 c.c. vial) containing 5 percent of sodium psylliate and 2 percent by weight of benzyl alcohol. That aqueous solution had a pH of 8.9 (enough 10% NaOH solution was added to achieve that level). The fracture was substantially cured in about three months after repeated injections.

EXAMPLE 19

An injectable liquefied composition containing 5 weight percent of sodium oleate, 1.5 weight percent of ethanol, enough sodium dihydrogen phosphate to obtain a pH of 9.8 and 50 ml. of sterile distilled water (q.s.). The liquefied composition was placed in several 2 c.c. ampoules. One of the ampoules was used to fill a hypodermic needle syringe of the type shown in FIG. 4. The liquefied solution was injected into the interface region between two bones in a leg of a horse to be fused. The treatment was not painful. X-rays indicated that "struts" were produced, giving rise to fixation and then complete fusion of the bones. The horse used the leg during the entire period of time. Another injection was made on the tenth day, and about every ten days thereafter until the surfaces of the bones were substantially fused after about two months.

EXAMPLE 20

Example 19 was repeated, except that the injectable liquefied composition containing the non-necrotic fatty acid compound of Example 19 was replaced with an injectable liquefied composition comprising an aqueous solution (5 c.c. vial) containing 5 percent of sodium psylliate and 2 percent by weight of benzyl alcohol. That aqueous solution had a pH of 8.9 (enough 10% NaOH solution was added to achieve that level). The surfaces of the bones were substantially fused in about two months after repeated injections.

EXAMPLE 21

Example 19 was repeated, except that the injectable liquefied composition containing the non-necrotic fatty acid compound of Example 19 was replaced with an injectable liquefied composition comprising an aqueous solution (2 c.c. vial) containing 2 percent of sodium ricinoleate. That solution had a pH between 8.2 and 8.5. The surfaces of the bones were substantially fused in about two months after repeated injections.

EXAMPLE 22

Example 19 was repeated, except that the injectable liquefied composition containing the non-necrotic fatty acid compound of Example 19 was replaced with an injectable liquefied composition comprising an aqueous solution (2 c.c. ampul) containing 5 percent ethylamine oleate and 2 percent benzyl alcohol. The surfaces of the bones were substantially fused in about two months after repeated injections.

EXAMPLE 23

Example 19 was repeated, except that the injectable liquefied composition containing the non-necrotic fatty acid compound of Example 19 was replaced with an injectable liquefied composition comprising an aqueous solution (2 c.c. ampoule) of 1 percent of sodium oleate and enough NaOH to bring the pH up to 9.1. The surfaces of the bones were substantially fused in about two months after repeated injections.

EXAMPLE 24

Example 19 was repeated, except that the injectable liquefied composition containing the non-necrotic fatty acid compound of Example 19 was replaced with an injectable liquefied composition comprising an aqueous solution (2 c.c. ampoule) of a 3 percent solution of sodium oleate and enough KOH to bring the pH up to 9.3. The surfaces of the bones were substantially fused in about two months after repeated injections.

EXAMPLE 25

Using the same injection technique and injectable liquefied composition of Example 19, a piece of bone was fused on both ends to another bone, thereby creating a splint.

EXAMPLE 26 a two-year old throughbred (colt) race horse had metacarpal periostetis (bucked shins) on the left and right fore legs. An injection was made into the site of each bucked shin using the injectable liquefied composition of Example 1 (in 10 cc. ampoules). The injection was made following the profile of proliferation, distributing 6 c.c. in each leg. There was no reaction to the injection and there was no follow up injection. The accepted healing time for bucked shins is 12 weeks (when not injected using the injectable liquid of this invention). The colt was exercised in 2 days, was pasture sound in 2 days, was returned to training in 10 days, was worked out on a track in 11 days and raced in 18 days. The colt was sound following the work out and race. This establishes the marked acceleration of healing using the injectable liquefied composition of this invention.

EXAMPLE 27

A two-year old throughbred (colt) race horse had metacarpal periostetis (bucked shins) on the left and right fore legs. (The bucked shins had been blistered and the colt rested for six weeks; after re-bucking, the bucked shins had been blistered again and then rested; but then the shins re-bucked again.) An injection was made into the site of each bucked shin using the injectable liquefied composition of Example 1 (in 10 c.c. ampoules). The injection was made following the profile of proliferation, distributing 8 c.c. in each leg. There was no reaction to the injection and there was no follow up injection. The accepted healing time for bucked shins is 12 weeks (when not injected using the injectable liquid of this invention). The colt was exercised in 1 day, was pasture sound in 2 days, was returned to training in 10 days and was worked out on a track in 10 days. The colt was sound following the work out. This establishes the marked acceleration of healing using the injectable liquefied composition of this invention.

EXAMPLE 28

A three-year old throughbred race horse (male) had (left fore leg third metacarpal periostetis (bucked shin). The affected area was swollen. (The bucked shin had been previously fired and blistered.) An injection was made into the site of the bucked shin using the injectable liquefied composition of Example 1 (in 10 cc. ampoules). The injection was made following the profile of proliferation, distributing 6 c.c. in the leg. There was someheat and swelling following the injection. There was no follow up injection. The accepted healing time for bucked shins is 12 weeks (when not injected using the injectable liquid of this invention). The colt was exercised in 10 days, and was returned to training in 10 days. The colt was sound following a work out This established the marked acceleration of healing using the injectable liquefied composition of this invention.

EXAMPLE 29

A three-year old throughbred race horse (female) left fore leg third metacarpal periostetis (bucked shin), specifically, the anterior surface one half way between the carpus and the first phalax. (The bucked shin had been previously blistered). An injection was made into the site of each bucked shins using the injectable liquefied composition of Example 1 (in 10 cc. ampoules). The injection was made following the profile of proliferation, distributing 6 c.c. in the leg. There was some heat and swelling over the area after the injection. There was no follow up injection. The accepted healing time for bucked shins is 12 weeks (when not injected using the injectable liquid of this invention). The colt was exercised in 12 days, and was returned to training in 12 days. The colt was sound following a work out. This establishes the marked acceleration of healing using the injectable liquefied composition of this invention.

EXAMPLE 30

A two-year old throughbred race horse (fully) had metacarpal periostetis (bucked shins) on the left and right fore legs. (The bucked shins had been previously fired.) An injection was made into the site of each bucked shin using the injectable liquefied composition of Example 1 (in 10 cc. ampoules). The injection was made following the profile of proliferation, distributing 6 c.c. in each leg. There was no reaction to the injection and there was no follow up injection. The accepted healing time for bucked shins is 12 weeks (when not injected using the injectable liquid of this invention). The colt was exercised in 2 days, was pasture sound in 2 days, was returned to training in 10 days and was worked out on a track in 18 days. The colt was sound following the work out, and has raced, won and remained sound. This establishes the marked acceleration of healing using the injectable liquefied composition of this invention.

EXAMPLE 31

A two-year old throughbred race horse (fully) had metacarpal periostetis (bucked shin) on the left fore leg. An injection was made into the site of each bucked shin using the injectable liquefied composition of Example 1 (in 10 cc. ampoules). The injection was made following the profile of proliferation, distributing 6 c.c. in the leg. There was no reaction to the injection and there was no follow up injection. The accepted healing time for bucked shins is 12 weeks (when not injected using the injectable liquid of this invention). The colt was exercised in 2 days, was pasture sound in 2 days, was returned to training in 10 days and was worked out on a track in 11 days. The colt was sound following the work out, has raced, won and remained sound. This establishes the marked acceleration of healing using the injectable liquefied composition of this invention.

EXAMPLE 32

2 cc of an injectable liquefied composition, the same as the one of Example 1, was injected into the site of ringbone of a horse. The ringbone was healed.

EXAMPLE 33

2 cc. of an injectable liquefied composition, the same as the one of Example 1, was injected into the site of osselets of a horse. The osselets healed.

EXAMPLE 34

Example 1 was repeated, with a fractured leg bone of a dog, except that the injectable liquefied composition containing the non-necrotic fatty acid compound of Example 1 was replaced with a cream (specifically a colloidal suspension). The cream contained 5 percent by weight of sodium oleate, 0.1 percent by weight of sodium phosphate (monobasic, monohydrate), 1.5 percent by weight of ethanol, 5 percent by weight of methylcellulose (60 HG 4000 cps), enough sodium hydroxide to obtain a pH of 9.8 and the remainder purified water (q.s.). The cream was injected into the fracture site. The fracture was substantially cured in a rapid time, faster than by natural healing. The healing seemed to be faster than when a liquefied composition of Example 1 was used. (a microscope examination of the healing process on a series of dogs showed the healing process to be microscopically normal.)

A control was also run using the procedure of Experiment 1. The control cream contained 10 percent by weight of methylcellulose (60 HG 4000 cps) and the remainder purified water (q.s.). The control cream was injected into the fracture site of a fractured leg bone of a second dog. The control or second dog was much slower in the healing of its fractured leg.

EXAMPLE 35

Before the flesh in the open reduction of a fractured dog was sutured up, a cream was applied to the open bone surface and into the open bone fracture site. The cream (a colloidal suspension) contained 5 percent by weight of sodium oleate, 0.1 percent by weight of sodium phosphate (monobasic, monohydrate), 1.5 percent by weight of ethanol, 5 percent by weight of methylcellulose (60 HG 4000 cps), enough sodium hydroxide to obtain pH of 9.8 and the remainder purified water (q.s.). The suturing was completed. The fracture was substantially cured in a rapid time, faster than by natural healing.

EXAMPLE 36

Example 1 was repeated, except that the sodium oleate of the injectable liquefied composition was replaced with an equal amount of monoethanolamine oleate. The fracture healing was substantially cured in a faster time than with normal healing.

EXAMPLE 37

A gelding having bone chips around a fractured leg site was operated on to remove the bone chips. The actual fracture site was injected with the liquefied composition of Example 1, and the surrounding area was sprayed with the liquefied composition of Example 1. The incision was sutured up in a normal manner. The fracture healed more rapidly than if natural healing had been allowed to occur, and no infection developed in the open reduction surgery site or incision.

EXAMPLE 38

Example 37 was repeated, except that the cream of Example 35 (instead of the liquefied composition of Example 1) was inserted into the fracture site and applied to the surrounding area. Slightly more rapid healing occured and no infection developed in the open reduction surgery site or incision.

EXAMPLE 39

A tooth was extracted. Immediatley after the extraction, the liquefied composition of Example 1 was placed in the extraction site (bone and tissue). No infection set in and no "dry socket syndrome" developed at the extraction site.

EXAMPLE 40

Example 40 was repeated, except that the cream of Example 35 was used instead of the liquefied composition of Example 1. No infection set in and no "dry socket syndrome" developed at the extraction site.

Another embodiment of this invention is described below.

When the fracture, break or non-union area (synovial fluid) has become polarized, the non-necrotic vascular sclerosing agents lose their permeability and their ability to perform their function in the healing process. By eliminating the polarity in the fracture, break or non-union area, the non-necrotic vascular sclerosing agents act in their normal manner in the healing of bone fractures, breaks or non-unions. Among the specific types of polarity which can be treated to remove such polarity are hematoma in fractures, breaks or non-unions which has become polarized, and synovial fluid in a fracture, break or nonunion occurring in a capsule which has become polarized. Also, this embodiment of this invention can be used to treat non-unions which occurred when the hematoma has become polarized and when, the fracture occurring within a capsule, the synovial fluid has become polarized.

This embodiment of this invention involves treating body surface (i.e., skin) near the bone surfaces in juxtaposition (e.g., fractures, breaks or nonunion of man or animal) with a liquefied composition containing a buffer system, the solution having a pH such that a pH of about 7.7 to about 6.5 is achieved in the fracture, break or nonunion interface region and immediately surrounding area thereof. This treatment is done when the pH of the interface region of the fracture has risen above about 7.7 (or below about 6.5). Also, at such pH's the lipids in the interace region become polarized. The polarized lipids are attracted to one another with a resultant mass. (This point concerning the lipids is gone into more detail below.) By adjusting the pH to a point within the pH range of about 7.7 to about 6.5, the lipid mass breaks up and the lipids become depolarized. This restores the lipids to their original state of permeability. The skin, hair, etc., is slightly acidic, so the pH of the solution containing the buffer system should be slightly higher than the desired pH in the fracture, break or non-union interface region. More specifically the pH of the solution containing the buffer system in that instance is up to 0.5 pH unit higher than the desired pH in the fracture, break or non union region. When the skin, etc., is properly cleaned, etc., before the treatment, the pH of the solution containing the buffer system need only be approximately that of the desired pH in the fracture, break or nonunion interface region.

Preferably the pH of the interface region of the break, fracture or non-union is between about 7.5 and about 6.9.

The solution containing the buffer system can be injected into the interface region, but this method is not preferred because it is not desirable to make any more injections than is absolutely necessary. The solution containing the buffer solution is preferably topically applied to the body surface near the fracture, etc. It can be applied in any manner, such as by wetted compress to which more solution is added as needed rubbed on, etc. The body surface can be sterilized or neutralized before application so as to reduce the natural acidity of the body surface which means the pH need not be raised to take in account the acidic nature of the body surface.

The liquefied composition contains a buffer and a fat solvent. Preferably the fat solvent is an aprotic solvent; the preferred aprotic solvent is dimethyl sulfoxide. The liquefied composition can contain water. The most preferred liquefied composition contains 10 percent of dimethyl sulfoxide, 10 percent of potassium acetate and 80 percent of sodium acetate.

In general, up to 80 percent of the fat solvent can be used, but preferably up to 20 percent fat solvent is used. The remainder is a buffer or buffer and water.

A more preferred alternative involves treating the body surface near the bone surfaces in juxtaposition with a liquefied composition comprised of a fat solvent (preferably an aprotic solvent), a buffer and a non-necrotic vascular sclerosing fatty acid compound, and which has a pH between about 6.5 and about 8.2. An acid or base (e.g., sodium hydroxide) can be used to adjust the pH to the desired range. Up to 10 percent by weight of the non-necrotic vascular sclerosing fatty acid compound is normally used. Up to 50 percent by weight of water can be used. When a substance such as ethanol is used up to 10 percent is used. Substances such as ethanol are used in such quantities when the non-necrotic vascular sclerosing fatty acid compound is not readily soluble in water or the fat solvent. The preferred composition of this narrower embodiment is 10 percent of diemethyl sulfoxide, 10 percent of water, 1.5 percent of ethanol, 5 percent of sodium oleate, 65 percent of sodium acetate and 8.5 percent of potassium acetate. The discussion of the above-described embodiment (only using a buffer and fat solvent) applies here. A suitable carrier for the non-necrotic vascular sclerosing fatty acid compound can be used—the preferred carrier is the above-described water-ethanol carrier.

The use of a non-necrotic vascular sclerosing fatty acid compound in the liquefied composition is very important as this allows the healing to begin almost at once whereas its absence means that healing is essentially delayed until the injection (discussed below) is actually made into the fracture site.

The liquefied composition containing a buffer and a fat solvent or a buffer, a fat solvent and a non-necrotic vascular sclerosing fatty acid compound can be used in a form such as a jelly, gel, cream, lotion or ointment; collectively called herein a cream. The cream can contain any conventional ingredients and is the same as the creams described above in the earlier described embodiments of this invention. The cream base can, for example: be a mixture of cetyl alcohol, an emulsifier such as lauryl sulfate, and water (preferred); include polyethylene glycols of different viscosities; a mixture of cetyl alcohol and propylene glycol; polyethylene glycol 400; a mixture of glyceryl monostearate, stearyl alcohol and polysorbate 80; a mixture of polyethylene glycol 4000 and propylene glycol monostearate; and a mixture (lotion) of glycerine and carbowax 400.

Any suitable means of topically applying the liquefied composition (including sprays, foams, suppositories and the above-described means) can be used.

One advantage of this invention is that it eliminates the need of whirlpooling during the heating period. Another advantage of this invention is that no injection need be made.

Lipides or lipids area class of fat-like compounds which are generally insoluble in water and are generally soluble in fat solvents.

The term fat solvent is well known. Examples of fat solvents which can be used in this invention are: dimethyl sulfoxide (preferred); methyl ethyl sulfoxide; $(C_2H_5)_2SO$; $(n-C_3H_7)_2SO$; ethyl ether; petroleum ether; benzene; acetone; n-hexane; extract naphtha or light petroleum fraction, mostly n-hexane; carbon disulfide; hydrogenated naphtha; toluene; xylene; coal-tar solvents petroleum spirits; phenols; naphthalenes; sulfonated derivitives of phenols, ketones, naphthalenes and hydrogenated coal-tar solvents; purified petroleum benzine; halogenated hydrocarbons, such as, chloroform, tetrachloroethane, pentachloroethane and carbon tetrachloride; trichloroethylene; and benzene soaps dissolved in amyl alcohol ether, chloroform, carbon tetrachloride or benzene. Mixtures of fat solvents can be used. The toxicity of the halogenated hydrocarbons generally makes them the least desirable of the fat solvents. The fat solvents can contain a minor amount of water. Lipids are generally freely miscible with or soluble in most solvents (except alcohols) at temperatures above the melting point of the solvent. The fat solvent must be liquid at the body temperature of the man or animal being treated.

The liquid carrier or fat solvent is preferably an aprotic solvent. Aprotic solvents are defined in Monograph 105 of the National Bureau of Standards. Aprotic solvents are almost devoid of acidic or basic properties, for example, aprotic solvents do not interact strongly with acidic solutes, such as, carboxylic acids, phenols and mineral acids, or with basic solutes such as, amines and derivatives of guanidine or pyridine. They are comparatively inert in character. Indifferent solvents or inert solvents are other names for aprotic solvents. In general, aprotic solvents are organic compounds.

There are generally two classes of aprotic solvents. The most preferred class of aprotic solvents are termed dipolar aprotic solvents and generally have a high dielectric constant that ranges from about 21 to about 46.5. The preferred aprotic solvent is demethyl sulfoxide =46). The most preferred fat solvent is dimethyl sulfoxide for its extraordinary ability to enhance the penetration of the buffer and other ingredients through an external membrane barrier of human and/or animal. Examples of other aprotic solvents in this class are nitrobenzene, methyl sulfoxide, benzonitrile, acetonitrile, dimethylacetamide, dimethylformamide, sulfolane (tetramethylenesulfone), acetone, N-methyl formamide, formamide, N-methyl propionamide, and mixtures thereof.

A second class of aprotic solvents generally have a dielectric constant in the range of about 2 to about 10. The aprotic solvents of this class generally are aliphatic hydrocarbons, aromatic hydrocarbons, and halogenated hydrocarbons. Such hydrocarbons can be saturated or unsaturated. Examples of such aprotic solvents are benzene, toluene, cyclohexane, o-xylene m-exylene, p-xylene, 2,2,4-trimethylpentane, mesitylene, decahydronaphthalene, phenylacetylene, tetrahydronaphthalene, chlorobenzene, o-dichlorobenzene and mixtures thereof.

Examples of mixtures of aprotic solvents are benzenedimethyl-sulfoxide, and benzene acetonitrile.

The fat solvent or aprotic solvent must be non-necrotic. The fat solvent or aprotic solvent should be at least miscible with the non-necrotic vasccular sclerosing fatty acid compound and/or water, if either or both are used. The fat solvent or aprotic solvent is effective from its solvent properties which help the other ingredients penetrate the external membrane barrier and the like of human and/or animal. Preferably, the fat solvent or aprotic solvent has good ability to alter membrane permeability and to thereby enhance penetration of the buffer, non-necrotic vascular sclerosing fatty acid compound, etc.

Dimethyl sulfoxide does no irreversible damage to the tissue. Dimethyl sulfoxide has a great ability (almost unique) to alter membrane permeability and to thereby greatly enhance penetration of physiologically-active and other types of agents. Another key feature of the use of dimethyl sulfoxide is its property of producing a very high rate of membrane penetration.

Dimethyl sulfoxide (DMSO) is

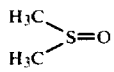

Dimethyl sulfoxide is a colorless liquid, completely miscrible with water and very hydroscopic, has a slightly bitter taste and practically no odor, boils at 189° C. (760 mm Hg) and has a melting pont of 18.45° C. The freezing point of dimethyl sulfoxide—water mixtures diminishes sharply to a minimum well below—70° C. at 5 percent dimethyl sulfoxide by weight. Dimethyl sufoxide is essentially nontoxic within a wide safety margin above the amounts used in this invention.

When a pH greater than 7 is desired, a weak-acid buffer system such as, boric acid—sodium borate, and $KH_2PO_4$—$Na_2HPO_4$ (including sometimes NaCl), can be used. When a pH less than 7 is desired, a buffer system comprised of a weak monoacid base and its salt can be used. Examples of useful buffers for use in the first feature of this invention are potassium acetate—sodium acetate (preferred), potassium dihydrogen phosphate—disodium hydrogen phosphate, potassium dihydrogen phosphate—sodium hydroxide, calcium dihydrogen phospate—potassium hydroxide, sodium dihydrogen phosphate, potassium hydroxide, borax-hydrochloric acid, tris)hydroxymethyl) aminomethane—hydrochloric acid, and calcium acetate—sodium acetate.

The term liquefied compositon includes, slurries, suspensions, solution, etc.

All of the components of any of the liquefied compositions of this invention must be substantially non-toxic in the amounts and under the conditions of use.

The pH of the liquefied composition when the non-necrotic vascular sclerosing fatty acid compound of the second feature of should be between about 8 and about 11, and preferably between 9 and about 10. Each non-necrotic vascular sclerosing fatty acid compound will produce a different pH at different concentration levels so non-toxic agents or buffers may be added to adjust the pH level, e.g., sodium hydroxide or dihydrogen sodium phosphate can be used.

The non-necrotic vascular sclerosing fatty acid compound can be any of those described above under the other embodiments of this invention. The preferred non-necrotic vascular sclerosing fatty acid compounds are ethanolamine oleate, and sodium oleate. The useful vascular sclerosing fatty acid compound must not cause the pathologic death of cells, or a portion of tissue or organ, resulting from irreversible damage to the nucleus.

The liquefied compositions which includes a non-necrotic vascular sclerosing fatty acid compound should contain between about 0.5 and about 10 percent by weight of the non-necrotic vascular sclerosing fatty acid compound, and preferably contain between about 1 and about 5 percent by weight of the non-necrotic vascular sclerosing fatty acid compound.

Examples of the liquid carrier for the non-necrotic vascular sclerosing are water, monyglycerides, diglycerides, etc. A mixture of water and ethanol is the preferred liquid carrier; salt (NaCl) can be added to make an isotonic aqueous solution as the liquid carrier.

Anodynes in amounts of up to and including about 5 percent by weight may be added to the liquefied compositions of both features of this invention. An anodyne is an agent which has the power to relieve pain . An example of a useful anodyne is benzyl alcohol. In general small amounts of antiseptics or anaesthetics can be used. Suitable preservations can be added in an amount not to exceed 0.5 percent by weight.

In some instances it may be necessary to use traction, but a cast as such is not used.

Where the synovial fluid treatment using a liquefied composition comprising a buffer and a fat solvent is completed, the bone fractures, breakes and nonunions themselves are treated. The process includes: aligning (only when necessary) the bone parts to position for setting; and then injecting at least one dosage of a liquefied composition comprised of a non-necrotic vascular sclerosing fatty acid compound and a liquid carrier into the site of the fracture, break or nonunion area of the bone. The injections are repeated until there is a substantially complete bone union. Preferbly another dosage is injected one or two weeks after the first dosage, and then every week or two thereafter as needed, until there is a substantially complete bone union. Preferably each dosage of the liquefied composition is injected into the site of the fracture, break or nonunion at its axis.

The non-necrotic vascular sclerosing fatty acid compound can be any of those disclosed above in the other embodiments of this invention. The preferred non-necrotic vascular sclerosing fatty acid compound is ethanolamine oleate, but when the sodium balance must be considered, the preferred compound is sodium oleate. When sodium oleate is used, the most preferred liquefied composition is comprised of 5 percent of sodium oleate, 1.5 percent of ethanol, enough sodium dihydrogen phosphate to obtain a pH of 9.8 and the remainder water.

The injection can be made as set out in FIG. 3 and the description above of FIG. 3.

(When the wing of the third phalanx or any other part thereof) of a horse is broken or fractured, the hoof can be drilled through and then a long needle inserted therethrough into the break, etc., or into the site of the break, etc. A liquefied composition containing a non-necrotic vascular sclerosing fatty acid compound is injected, via the long needle on the hypodermic needle, into the break, etc., or into the site of the break, etc. The buffer—fat solvent treatment of this invention cannot be used in this type of situation.)

Instead of injecting the liquefied composition containing the non-necrotic vascular sclerosing fatty acid compound, the latter can be introduced into the bone fracture site to healed by applying it to the adjacent skin in mixture with dimethyl sulfoxide (by itself or in the form of a cream).

This invention also includes an admixture of dimethyl sulfoxide, a buffer and a non-necrotic vascular sclerosing unsaturated fatty acid compound.

EXAMPLE 40

A horse was purchased two weeks following his fracture of the accessory carpal during a race. The knee had very little edema and/or heat. An injection was made at the axis of the main fracture sight with an injectable liquefied composition containing 5 weight percent of sodium oleate, 1.5 weight percent of ethanol, enough sodium dihydrogen phosphate to obtain a pH of 9.8 and the remainder water. Another injection was made with the same composition two weeks later at the axis of the remaining fracture sights. Within five weeks the healing was approximately 85 percent complete. This happened to be a particular fractious colt and his exercise consisted of being hand walked daily for a half hour prior to be given freedom in an enclosed 40 foot circle. New help misunderstood instructions and turned the colt loose in a 1.2 acre stud paddock. New found freedom and slippery grass resulted in the colt, slipping and falling, and as chance would have it, the colt twisted the fractured leg when falling and then used it unwisely in getting to his feet. As a result the colt not only refractured the accessory carpal, but sprained the knee as well. Standard procedure of whirlpooling and sweating reduced the edema and heat. At the end of two weeks, the fracture was injected with the above-described injectable liquefied composition (containing sodium oleate). Two weeks later radio graphs showed that no healing had taken place and the knee had become somewhat hardened.

It was thought that if the pH could be restored to 7.5, it would be possible to stabilize the fluid and, in turn, the fatty acids could function in a normal manner within a normal bioelectric field. A liquefied composition buffered at 8.5 was prepared; the theory being that as the drive through the acid condition of the hair, epidermis and dermis was made, the liquefied composition would arrive in the synovial fluid capsule at a level condusive to adjusting the pH to about 7.5. The liquefied composition contained 10 percent DMSO and 90 percent saline solution. Applicant took into consideration the ability of the properties of DMSO to aid in the dissolving of the lipids; however, because of the ratio, applicant postulated that for this experiment, applicant would predict the alteration of the pH resulting from the saline solution. The knee was painted twice daily and there was some reduction of edema and softening of tissue. The synovial fluid was aspirated again and the pH was 7.9. It was obvious that the 8.5 pH liquefied solution was in error, and so a second liquefied composition was prepared. In order to avoid what could be a pseudo-edema created from an over abundance of sodium in relationship to the potassium balance, the second liquefied composition contained 10 percent dimethyl sulfoxide, 10 percent potassium acetate, 80 percent of sodium acetate and had a pH of 7.9. This was applied twice daily and it dramatically produced the desired effect. The knee softened and the edema dissipated. It is interesting to note that as the swelling abated a jelly like filling followed the sheath of the interosseous ligament approximately ⅔ of its length prior to dissipation. One cannot help but ponder that in some cases the resultant configuration of the ailment known as a "bowed tendon" could be contributed to the initial trauma occurring in the carpal canal. In other words should the lipids of the canal become polarized they would not only have an alteration of their bio-electric field in regards to permeability but as they would attract one another the mass would in turn be attracted to the weakened area of the sheath which through disrupted potential outflow from the injured area and would then form a "cesspool" or collection sight.

In approximately four weeks the knee had resumed a normal configuration assuming that the tissues, synovial fluid and bio-electric field were once again in balance, 1 cc of the above-described injectable liquefied composition (containing sodium oleate) was injected at the fracture sight. The fracture healed much faster than by conventional means.

This invention still further involves another embodiment which includes process of accelerating the death and destruction of bony cells producing unwanted new bone proliferation, say, both without and within joint capsules. This is not a surgical procedure but it is accomplished by injecting a dosage of a liquefied composition comprised of a vascular sclerosing anionic agent and a liquid carrier into and around abnormal new bone proliferations. Subsequent dosages are preferably administered approximately every five days, but the injection interval depends on the density and location of the calcium deposits. This injection method is also used to remove unwanted new bone proliferation which occur immediately around the region of or in the perimeter of a broken bone (or fractured bone or non-union). This embodiment can be used to treat both man and animal. In a sense, this embodiment involves the absorption of abnormal new bone proliferation. The pertinent portions of applicant's copending application Ser. No. 123,830 are incorporated herein by reference.

Each dosage contains between about 0.1 and about 10 c.c., although a 2 c.c. dosage is normally used. The liquefied composition should contain about 0.5 and about 5 weight percent of a vascular sclerosing anionic agent, and preferably between about 1 and about 3 percent of a vascular sclerosing anionic agent. The liquefied composition should have a pH between 6 and 10, and preferably between about 7 and about 8.1, and most preferably about 7.2.

The preferred liquefied composition is comprised of an aqueous solution of 3 weight percent of sodium tetradecyl sulfate. The preferred liquefied composition contains 2 percent of benzyl alcohol, is buffered with disodium phosphate and is adjusted with sodium dihydrogen or sodium hydroxide to a pH of about 7 to about 8.1.

This embodiment is often used before a fracture, break or non-union is treated using the injectable liquefied composition of this invention (described above).

The process of this embodiment can also be used to remove arthritic spurs or deposits or growth which result from certain types of arthritis, and can further be used to perform what is commonly known as cosmetic surgery.

This invention also involves the treatment of psoriasis to alleviate the itching associated therewith, to eliminate the flaking associated therewith, to produce a natural, soft skin in the psoriasis sites, and to cure or heal the psoriasis. This is done by treating the psoriasis sites with a composition containing a non-necrotic unsaturated fatty acid compound having one double bone (other fatty acid compounds can be used, but they are not as satisfactory in results). The preferred unsaturated fatty acid is sodium oleate. The composition should be liquefied and preferably in an ointment or salve form. The salve carriers can be those described above as gel or cream bases. The preferred base is acid mantle because it melts with body heat. The unsaturated fatty acid is preferably present in an amount between 10 and 80 percent by weight and most preferably in an amount of 50 percent by weight. Preferably the composition contains minor amounts of vitamins A and D (0.01 to 2 percent by weight of each). Foams and sprays can be used.

Psoriasis is an idiopathic chronic inflammatory skin disease characterized by the development of red patches covered with silvery white imbricated scales, or also described as, a chronic recurrent papulosquamous dermatosis, the distinctive lesion being a silvery gray scaling papule or plaque. Itching is very bad with psoriasis. After the flakes come off the skin is still flaky—the skin is not "new" even though the redness may eventually disappear.

Applicant theorizes that psoriasis involves a causation that involves a high cholesterol level, lessions which become fungi site and a change in the bioelectric field. The active ingredient (fatty acid compound) helps to alleviate and prevent these causation factors. This is due in part to the pH change brought about by the active ingredient.

In one case, a woman having chronic psoriasis on the hand has been treated unsuccessfully for a number of years. The psoriasis site (circular) was treated with a salve containing 50 percent by weight sodium oleate, minor amounts of vitamin A and D, and an inert neutral salve carrier or base (i.e., acid mantle). After seven days the circular psoriasis site was reduced to a "new moon" shape. The skin in the other region was natural looking and soft (not tan or "liver spots" like after when the top drops off in the usual case). The treatment with the salve prevented the flaking that normally occurs with psoriasis, and, even more importantly, the terrible itching that occurs with psoriasis immediately stopped (within 15 minutes).

Besides psoriasis, the salve of this invention which contains the fatty acid compound can be used to treat dermatoses, such as, exfoliative dermatitis, eczema, eczematous dermatitis, dermatitis seborrheica, dermatitis atrophicans, otitis externa, lichen planus, intertrigo, anogenital pruritus, lichen simplex chonicus, sun burn, diaper rash, insect bites, athletes foot, and dermatitis venenata (poison ivy, poison oak and the like).

What is claimed is:

1. The liquefied composition consisting essentially of an effective amount of a non-necrotic sclerosing fatty acid salt, an effective amount of ethyl alcohol, a buffering agent, and a water carrier, said salt prepared from an unsaturated fatty acid having one double bond and from an alkali metal or an alkaline earth metal or an alkali metal compound or an alkaline earth metal compound, and said liquefied composition having a pH between 9 and 11.

2. The liquefied composition as claimed in claim 1 wherein said fatty acid compound is calcium oleate.

3. The liquefied composition as claimed in claim 1 wherein said fatty acid compound is potassium oleate.

4. The liquefied composition as claimed in claim 1 wherein 1 to 10 percent of said non-necrotic fatty acid salt and 0.1 to 5 percent of the ethanol is present.

5. The liquefied composition as claimed in claim 4 wherein the pH is between 9 and 10 and enough of the buffer is present to adjust the pH to the stated range.

6. The liquefied composition as claimed in claim 5 wherein said unsaturated fatty acid is unsubstituted and contains 14 to 22 carbon atoms.

7. The liquefied composition as claimed in claim 6 wherein said salt is prepared from an alkali metal or an alkali metal compound.

8. The liquefied composition as claimed in claim 7 wherein said alkali metal is sodium.

9. The liquefied composition as claimed in claim 7 wherein said alkali metal is potassium.

10. The liquefied composition as claimed in claim 1 wherein said unsaturated fatty acid is unsubstituted and contains 14 to 22 carbon atoms.

* * * * *